ns Patent [19] [11] 4,076,730
Strike [45] Feb. 28, 1978

[54] PROSTAGLANDIN DERIVATIVES
[75] Inventor: Donald P. Strike, St. Davids, Pa.
[73] Assignee: American Home Products Corporation, New York, N.Y.
[21] Appl. No.: 494,118
[22] Filed: Aug. 2, 1974

Related U.S. Application Data

[60] Division of Ser. No. 384,769, Aug. 1, 1973, Pat. No. 3,845,042, which is a continuation-in-part of Ser. No. 282,200, Aug. 21, 1972, abandoned.

[51] Int. Cl.$^2$ .................. C07C 121/46; C07D 309/22
[52] U.S. Cl. ...................... 260/345.7 P; 260/345.8 P; 260/464
[58] Field of Search .................. 260/464, 345.7, 345.8, 260/240 R, 345.7 P, 345.8 P Primary Examiner—Joseph Paul Brust
Attorney, Agent, or Firm—David E. Frankhouser

[57] ABSTRACT

Prostaglandin compounds substituted at the 11-position, and possessing broncho-dilating and hypotensive activity are prepared from PGA$_2$ and its esters and 15-epimers.

1 Claim, No Drawings

PROSTAGLANDIN DERIVATIVES

This is a division of U.S. application Ser. No. 384,769, filed Aug. 1, 1973, now U.S. Pat. No. 3,845,042; which in turn is a continuation-in-part of U.S. application Ser. No. 282,200, filed Aug. 21, 1972, and now abandoned.

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation, the ability to reduce gastric secretion, to modify muscle tone, as well as the ability to raise or lower blood pressure.

The present invention concerns prostaglandin compounds in which the 11-position (using the prostanoic acid numbering system) is variously substituted with chemical groupings not found in nature.

SUMMARY OF THE INVENTION

The invention sought to be patented in a first composition aspect resides in the concept of a chemical compound of the structure

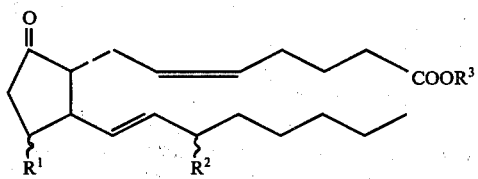

wherein $R^1$ is nitromethyl, vinyl, phenyl, methyl, benzyl, cyano, mercapto, (lower)alkylthio, phenylthio, carboxycyanomethyl, carb(lower)alkoxycyanomethyl, dicarboxymethyl, dicarb(lower)-alkoxymethyl, dicyanomethyl, or carbamoylcyanomethyl; $R^2$ is hydroxy, tetrahydropyranyloxy, or acetoxy; and $R^3$ is hydrogen or (lower)alkyl.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the first composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in a second composition aspect resides in the concept of a chemical compound of the structure

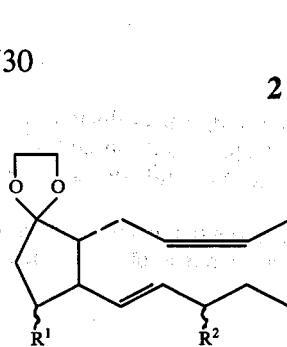

wherein $R^1$ is cyano, carboxy, carbamoyl, formyl, hydroxymethyl, acetyl, 1-hydroxyethyl, or nitromethyl; $R^2$ is hydroxy or acetoxy, and $R^3$ is hydrogen or lower alkyl.

The tangible embodiments of the second composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the second composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in a third composition aspect resides in the concept of a chemical compound of the structure

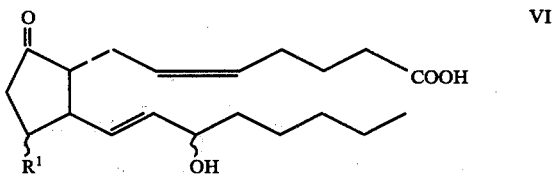

wherein $R^1$ is carboxy, acetyl, carbamoyl, hydroxymethyl, or 1-hydroxyethyl.

The tangible embodiments of the third composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the third composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in a fourth composition aspect resides in the concept of a chemical compound of the structure

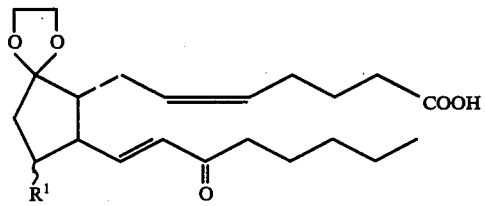

wherein $R^1$ is nitromethyl or cyano.

The tangible embodiments of the fourth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fourth composition aspect of the invention possess the inherent applied use characteristic of being intermediates in the synthesis of other compositions of the invention.

The invention sought to be patented in a fifth composition aspect resides in the concept of a chemical compound of the structure

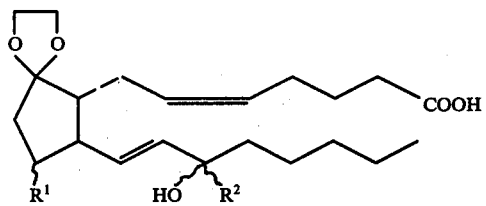

wherein $R^1$ is nitromethyl or cyano and $R^2$ is methyl or phenyl.

The tangible embodiments of the fifth composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the fifth composition aspect of the invention possess the inherent applied use characteristic of being intermediates in the synthesis of other compositions of the invention.

The invention sought to be patented in a sixth composition aspect resides in the concept of a chemical compound of the formula

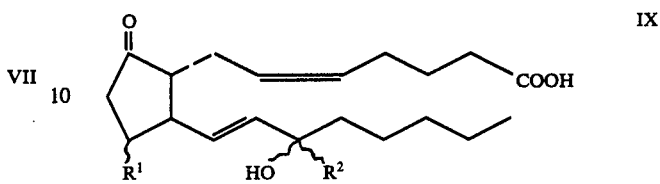

wherein $R^1$ is nitromethyl or cyano and $R^2$ is methyl or phenyl.

The tangible embodiments of the sixth composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the sixth composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in a seventh composition aspect resides in the concept of a chemical compound of the formula

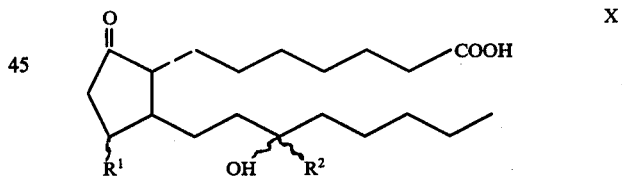

wherein $R^1$ is nitromethyl or cyano and $R^2$ is methyl or phenyl. The tangible embodiments of the seventh composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the seventh composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in an eighth composition aspect resides in the concept of a chemical compound of the formula

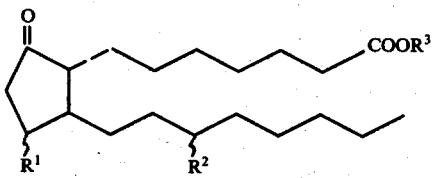

IV wherein $R^1$ is carbamoyl, methyl, carboxy, benzyl, nitromethyl, phenyl, cyano, carb(lower)alkoxycyanomethyl, carboxycyanomethyl, dicarb(lower)alkoxymethyl, dicarboxymethyl, hydroxymethyl, acetyl, or 1-hydroxyethyl; $R^2$ is hydroxy, tetrahydropyranyloxy or acetoxy; and $R^3$ is hydrogen or (lower)alkyl.

The tangible embodiments of the eighth composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the eighth composition aspect of the invention possess the inherent applied use characteristic of exerting bronchodilating and hypotensive effects upon administration to warm-blooded animals as evidenced by pharmacological evaluation according to standard test procedures, and, in addition, are useful as intermediates in the synthesis of other compositions of the invention.

The invention sought to be patented in a ninth composition aspect of the invention resides in the concept of a chemical compound of the formula

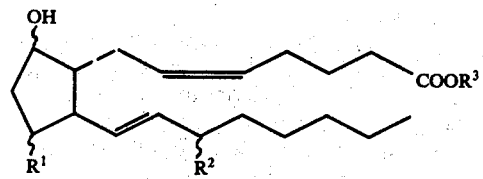

III wherein $R^1$ is mercapto, nitromethyl, vinyl, phenyl, methyl, phenyl, benzyl, cyano, (lower)alkylthio, phenylthio, carboxycyanomethyl, dicarboxymethyl, dicyanomethyl, or carbamoylcyanomethyl; $R^2$ is hydroxy or tetrahydropyranyloxy; and $R^3$ is hydrogen or (lower)alkyl.

The tangible embodiments of the ninth composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The tangible embodiments of the ninth composition aspect of the invention possess the inherent applied use characteristic of exerting bronchodilating and hypotensive effects upon administration to warm-blooded animals as evidenced by pharmacological evaluation according to standard test procedures, and, in addition, are the synthesis of other compositions of the invention.

DESCRIPTION OF THE PREFERRED EMBODIMENTS

In describing the synthesis of the compositions of the invention, reference will be made to the following figure wherein the formulae representing the various aspects of the invention are assigned Roman numerals for purposes of identification. The numerals assigned are the same as those indicated above in the Summary of the Invention, and the definitions of $R^1$, $R^2$, and $R^3$ are the same as those which were denoted for each corresponding aspect.

The starting materials of formula I are either known compounds of simple derivatives thereof readily prepared by means known to those skilled in the art of chemistry. Thus the starting materials 15-epiprostaglandin-$A_2$ and its methyl ester, acetate, may be isolated from *Plexaura homomalla* as described by Weinheimer and Spraggins, Tetrahedron Letters, 59, 5185 (1969); prostaglandin-$A_2$ (Prostaglandins, Bergstrom et al., ed., Interscience Publishers, 1967), and prostaglandin-$A_2$, methyl ester (Bundy et al., Annals of the N.Y. Academy of Sciences, 180, 76 [1971]) and also known in the art. Starting materials where $R^2$ is tetrahydropyranyloxy may be readily prepared by, for example, reacting the corresponding 15-hydroxy starting material with dihydropyran in the presence of p-toluenesulfonic acid, and prostaglandin-$A_2$, methyl ester, acetate, may be prepared from prostaglandin-$A_2$, methyl ester by, for example, treatment with acetic anhydride in the presence of pyridine.

Figure 1

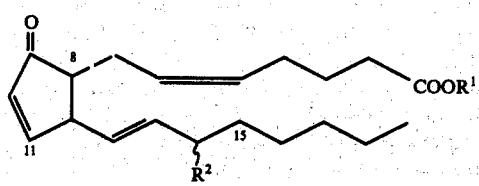

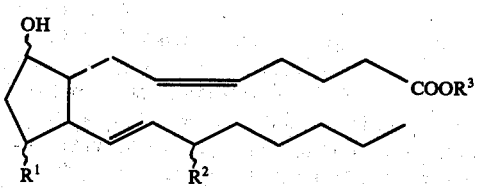

-continued

Figure 1

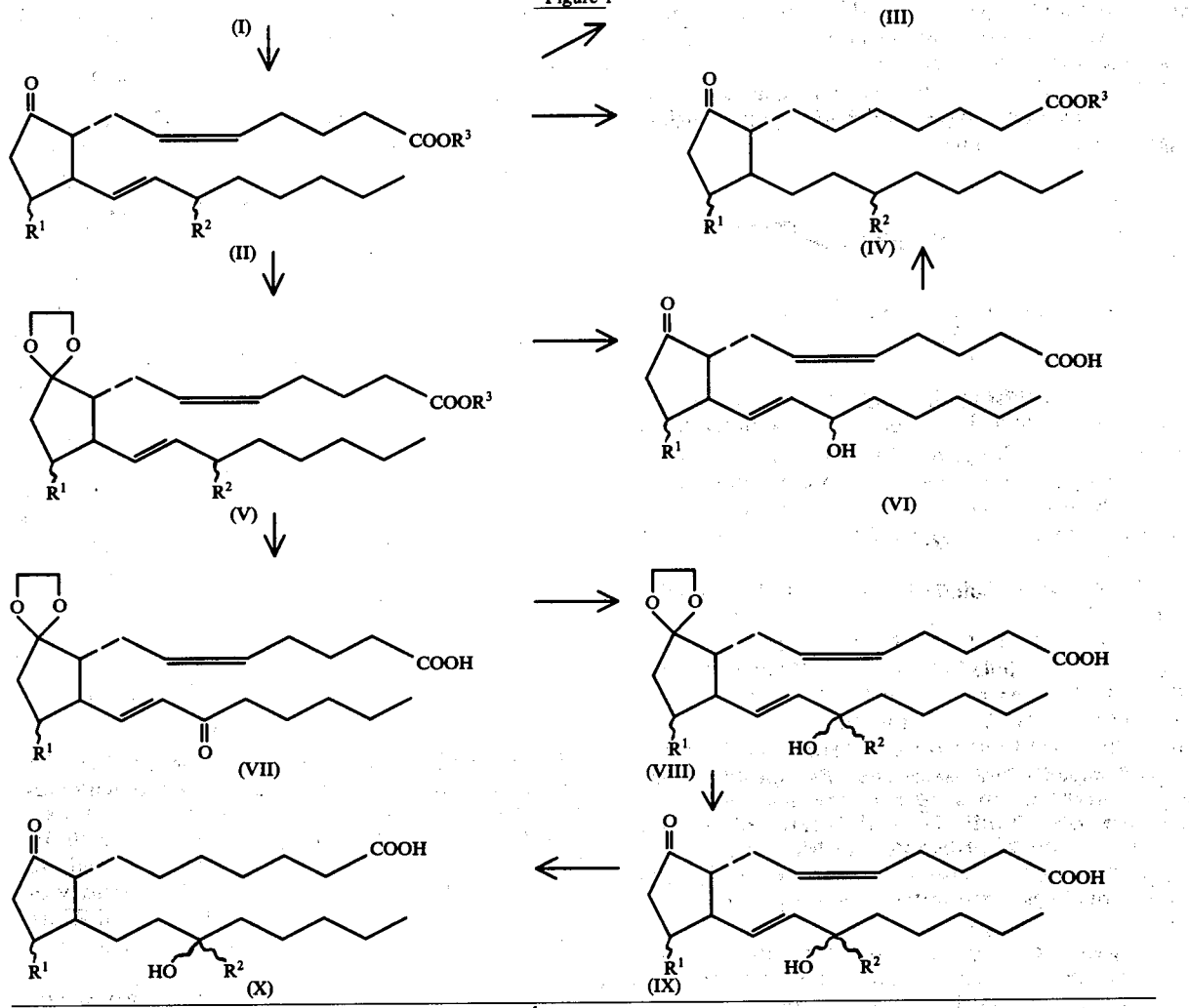

Compounds of formula II are prepared from the starting materials (I) by 1,4-conjugate addition to the α,β-unsaturated ketone system. This addition is accomplished either by treatment with Grignard reagents in the presence of a cuprous compound, such as cuprous chloride, or by treatment with a Michael reaction donor in the presence of a strong base, or by treatment with a thiolating agent such as sodium sulfide, thiophenol, or ethanethiol. Where the compounds of formula II contain ester or ether groups, these may be hydrolyzed to afford the corresponding free hydroxy-acid compounds.

Compounds of formula III are produced by treatment of the corresponding formula II compounds with a hydride reducing agent such as sodium borohydride. The compounds of formula IV are produced by hydrogenation of the corresponding formula II or formula VI compounds, for example, by hydrogenation in the presence of palladium on carbon.

Ketal compounds of formula V are prepared by ketalization by art-recognized methods, such as treatment with ethylene glycol in the presence of p-toluenesulfonic acid. Where the formula V compounds are esters, they may be hydrolyzed, for example, with methanolic sodium hydroxide to afford the corresponding free hydroxy-acids. Compounds of formula V wherein $R^1$ is carbamoyl or carboxyl are prepared by hydrolyzing compounds V wherein $R^1$ is cyano, for example, by hydrolysis with aqueous methanolic sodium hydroxide at reflux temperature followed by separation of the two products, for example, by silica chromatography. Compound V wherein $R^1$ is hydroxy-methyl is produced by treating V wherein $R^1$ is cyano with triethoxyhydride followed by aqueous hydrolysis, preferably acidic, to give V where $R^1$ is formyl, followed by reduction, for example, with sodium borohydride. Compound V where $R^1$ is acetyl is prepared by treatment of V wherein $R^1$ is cyano with methyl magnesium bromide followed by aqueous acid. The acetyl compound may be reduced, for example, with sodium borohydride, to produce V wherein $R^1$ is 1-hydroxyethyl.

Compounds of formula VI are prepared by deketalization by art-recognized methods of compounds of formula V, for example, by treatment with hydrochloric acid in tetrahydrofuran. The 15-ketone compounds of formula VII are prepared by oxidation of compounds of formula V with Jones reagent. Compounds of formula VIII are prepared by reaction of Formula VII compounds with methyl or phenyl Grignard reagent. Compounds of formula IX are prepared by deketalization of compounds of formula VIII, for example, with hydrochloric acid or perchloric acid in tetrahydrofuran. Compounds of formula X are produced by hydrogenation of compounds of formula IX, for example, by hydrogenation and in the presence of palladium on carbon.

It will be apparent to those skilled in the art of chemistry that the carbon atoms to which substituents $R^1$ and $R^2$ are attached in the compositions of the invention are asymmetric carbon atoms, and as a consequence these positions can be either of two epimeric configurations. The symbol $\sim\sim$ where used in this specification is to indicate that both possible configurations at each pariticular position is intended and is included within the scope of the invention. Substituents $R^1$ are introduced in the preparation of the compounds of the invention, and their introduction results in the formation of a mixture of the two epimeric forms with reference to that position. In compounds of formulae VIII, IX, and X, substituents $R^2$ are similarly introduced at a previously non-asymmetric center, and again both possible configurations are formed in mixture. In the other compounds of the invention, the 15-position (to which $R^2$ is attached) is asymmetric in the starting material and remains so through the formation of the desired product; as a result, the configuration at this position in the product will depend on the configuration in the starting material. Where, in the invention, epimeric mixtures are formed, they can, if desired, be separated by various means well-known in the art, such as chromatography.

Various compounds of the invention bear hydroxyl or carboxyl groups which can be readily esterified by art-recognized means to produce simple esters thereof; similarly, various compounds bear carboxyl groups and can be readily converted to their alkali metal salts or a salt of a pharmacologically acceptable cation derived from ammonia or a basic amine. All such esters and salts are full equivalents of the subject matter particularly claimed.

Where used in this specification and claims, the terms "(lower)alkyl" and "(lower)alk-" include straight and branched chain hydrocarbon radicals of from 1 to about 6 carbon atoms.

In using the compounds of the invention to produce brochodilating effects in warm-blooded animals, they may be administered in a variety of dosage forms: oral, injectable, and oral inhalation. Oral inhalation administration is a preferred route because of its rapid onset of action, great potency, and specificity of action. The particular dosage to obtain the bronchodilating effect will vary with the particular compound employed, the particular animal involved, and the degree of bronchodilation desired. In the guinea pig, by the oral inhalation route, the dose to produce bronchodilation is from about 0.2 micrograms to about 100 micrograms, and preferably from about 5 to about 50 micrograms. The bronchodilation produced upon oral inhalation administration can be observed by the method of Rosenthale et al., Int. Arch. Pharmacol., 172, 91 (1968).

In the use of the compounds of the invention to produce hypotensive effects in warm-blooded animals, administration by the injectable route is preferred, preferably the intravenous route.

The following examples further illustrate the best mode contemplated by the inventors of making the compositions of the invention.

EXAMPLE 1

7-[2-(3-S-Hydroxy-1-Octenyl)-5-Oxo-3-Cyclopenten-1-Yl]-5-Heptenoic Acid, Methyl Ester A solution of 16.0 g. of $PGA_2$ in 200 ml. of ether was treated with excess diazomethane in ether and kept at 25° for 1 hour. The excess diazomethane was decomposed with acetic acid and the mixture diluted with ether, washed with water and dried over sodium sulfate. Evaporation of the solvent gave 17.0 g. of the title product as an oil, $\lambda_{max}^{film}$ 3.0, 3.45, 5.75, 5.85 $\mu$.

EXAMPLE 2

7-[2-(3-S-[Tetrahydropyran-2-Yloxy]-1-Octenyl)-5-Oxo-3-Cyclopenten-1-Yl]-5-Heptenoic Acid A solution of 10.0 g. of $PGA_2$, 4.0 g. of dihydropyran and 0.06 g. of p-toluenesulfonic acid in 300 ml. of benzene was stirred at 25° for one hour. The reaction mixture was diluted with ether, washed with water and dried over sodium sulfate. Evaporation and silica chromatography of the residue with 30% ethyl acetate in hexane gave 4.4 g. of the title product as an oil, $\lambda_{max}^{film}$ 3.45, 5.85, 6.3, 9.8, 10.3 $\mu$; $\lambda_{max}^{95\% EtOH}$ 218 m$\mu$ ($\epsilon$ 9,600).

EXAMPLE 3

7-[2-(3-S-[Tetrahydropyran-2-Yloxy]-1-Octenyl)-5-Oxo-3-Cyclopenten-1-Yl]-5-Heptenoic Acid, Methyl Ester A solution of 1.0 g, of 7-[2-(3-S-[tetrahydropyran-2-yloxy -1-octenyl)-5-oxo-3-cyclopenten-1-yl]-5-heptenoic acid in 20 ml. of ether was treated with excess diazomethane in ether and the mixture kept at 25° for 0.5 hours. After destroying the excess diazomethane with acetic acid, the solution was washed with water and dried over sodium sulfate. Evaporation of the solvent gave 0.95 g. of the title product as an oil, $\lambda_{max}^{film}$ 3.45, 5.8, 5.9, 9.7, 10.3 $\mu$; $\lambda_{max}^{95\% EtOH}$ 218 m$\mu$ ($\epsilon$ 9,600). NMR: $\delta$ 7.55 (dd, J=1.5, 6.0, 11—H), 6.20 (dd, J=2.2, 6.0, 10—H), 5.50 (M, 4, olefinic), 4.68 (M, 1, O—CH—O), 3.68 (s, 3, $OCH_3$) ppm. Mass spectrum: M+ at m/e 432 (theory 432), M+—$OCH_3$ at m/e 401.2746 (theory 401.2690).

EXAMPLE 4

7-[2-(3-R-[Tetrahydropyran-2-Yloxy]-1-Octenyl)-5-Oxo-3-Cyclopenten-1-Yl -5-Heptenoic Acid A solution of 3.936 g. of 15-epi-$PGA_2$ and 1.5 g. of dihydropyran in 100 ml. of benzene was treated with 25 mg. of p-toluenesulfonic acid and the mixture stirred at 25° under nitrogen for 1 hour. The reaction mixture was diluted with ether, washed with water and dried over sodium sulfate. The solvent was evaporated and the residue chromatographed on silica and eluted with 30% ethyl acetate in hexane to obtain 3.75 g. of the title product as an oil, $\lambda_{max}^{film}$ 3.4, 5.8, 6.3, 9.8, 10.25 $\mu$; $\lambda_{max}^{95\% EtOH}$ 219 m$\mu$ ($\epsilon$ 9,800). NMR:$\delta$ 7.55 (dd, J=2.2, 6.0, 11—H), 6.25 (dd, J=1.5, 6.0, 10—H), 5.4$\beta$ (M, 4, olefinic), 4.72 (bs, 1, O—CH—O) ppm. Mass spectrum: M+—OPy at m/e 317.2099 (theory 317.2116).

EXAMPLE 5

7-[2-(3-S-Hydroxy-1-Octenyl)-5-Oxo-3-Cyclopenten-1-YL]-5-Heptenoic Acid, Methyl Ester, Acetate A solution of 17.0 g. of 7-[2-(3-S-hydroxy-1-octenyl)-5-oxo-3-cyclopenten-1-yl]-5-heptenoic acid, methyl ester, in 300 ml. of pyridine and 30 ml. of acetic anhydride was stirred at 25° for 6 hours. The reaction mixture was concentrated under vacuum, diluted with ether, washed with water and dried over sodium sulfate. Evaporation of the solvent and silica chromatography of the residue with 15% ethyl acetate in hexane gave 15.3 g. of the title product as an oil, $\lambda_{max}^{film}$ 3.45, 5.7, 5.8, 6.3, 8.0, 9.25, 10.25 μ.

EXAMPLE 6

7-[2-(3-R-Hydroxy-1-Octenyl)-3-Nitromethyl-5-Oxocyclopentyl]-5-Heptenoic Acid, Methyl Ester, Acetate A solution of 13.4 g. of 15-epi-PGA$_2$, methyl ester, acetate and 37.3 ml. of nitromethane in 250 ml. of methanol was treated with 1.485 g. of sodium methylate and the mixture stirred at 25° under nitrogen for 2 hours. The reaction mixture was diluted with ether, washed with water and dried over sodium sulfate. Evaporation and chromatography of the residue on silica with 40% ethyl acetate in hexane gave 8.9 g. of the title product as an oil, $\lambda_{max}^{film}$ 3.4, 5.7, 6.4, 8.0, 9.8, 10.3 μ. NMR: δ 5.60 (M, 2, 13 and 14—H), 5.37 (M, 3, 5—6—15—H), 4.45 (M, 2, CH$_2$NO$_2$), 3.67 (S, 3, OCH$_3$), 2.06 (s, acetate) ppm.

EXAMPLE 7

7-[2-(3-R-Hydroxy-1-Octenyl)-3-Nitromethyl-5-Oxocyclopentyl]-5-Heptenoic Acid

A solution of 0.60 g. of 7-[2-(3-R-hydroxy-1-octenyl)-3-nitromethyl-5-oxocyclopentyl]-5-heptenoic acid, methyl ester, acetate in 20 ml. of methanol was treated with 15 ml. of 1N sodium hydroxide and the mixture stirred at 25° under nitrogen for 0.5 hours. The reaction mixture was added to water, acidified with hydrochloric acid and extracted with ether. After washing with water and drying over sodium sulfate, the extract was evaporated and the residue chromatographed on silica. Elution with 30% ethyl acetate in hexane gave 0.653 g. of the title product as an oil, $\lambda_{max}^{film}$ 3.0 (shoulder), 3.4, 5.7, 5.8, 6.4, 7.2, 10.3 μ. NMR: 6.70 (s, 2, OH), 5.60 (M, 2, 13 and 14—H), 5.40 (M, 2, 5 and 6—H), 4.45 (M, 2, CH$_2$NO$_2$), 4.15 (M, 1, 15—H) ppm. Mass spectrum: M$^+$ at m/e 395 (theory 395), M$^+$—H$_2$O at m/e 377.2224 (theory 377.2201).

EXAMPLE 8

7-[2-(3-R-[Tetrahydropyran-2-Yloxy]-1-Octenyl)-5-Oxo-3-Vinylcyclopentyl]-5-Heptenoic Acid A solution of 5.75 ml. of 3.35 M vinyl magnesium chloride in 15 ml. of THF was added dropwise to an ice-cooled mixture of 0.65 g. of 7-[2-(3-R-[tetrahydropyran-2-yloxy]-1-octenyl)-5-oxo-3-cyclopenten-1-yl]-5-heptenoic acid and 1.27 g. of cuprous chloride in 25 ml. of THF with stirring under nitrogen. After stirring at 0° for 1 hour, the reaction mixture was added to aqueous ammonium chloride solution and extracted with ether. After washing with water and drying over sodium sulfate, the extract was evaporated and the residue chromatographed on silica. Elution with 20% ethyl acetate in hexane gave 0.27 g. of the title product as an oil, $\lambda_{max}^{film}$ 3.45, 5.75, 5.85, 6.1, 9.8, 10.25, 11.0 μ. NMR: δ 4.7–5.7 (M, 7, olefinic), 4.75 (bs, O—CH—O) ppm. Mass spectrum: M$^+$—OPy at m/e 345.2433 (theory 345.2429).

EXAMPLE 9

7-[2-(3R-Hydroxy-1-Octenyl)-5-Oxo-3-Vinylcyclopentyl]-5-Heptenoic Acid

An ice-cooled solution of 0.30 g. of 7-[2-(3-R-[tetrahydropyran-2-yloxy]-1-octenyl)-5-oxo-3-vinylcyclopentyl]-5-heptenoic acid in 20 ml. of THF was treated with 5.0 ml. of hydrochloric acid and the mixture stirred at 0° under nitrogen for 5 minutes. The reaction mixture was diluted with water, extracted with ether and the extract washed with water and dried over sodium sulfate. Evaporation and silica chromatography of the residue with 30% ethyl acetate in hexane gave 0.13 g. of the title product as an oil, $\lambda_{max}^{film}$ 3.0, 3.45, 5.8, 6.1, 10.3, 10.95 μ. NMR: δ 4.8–5.9 (M, 7, olefinic), 4.2 (M, 1, 15—H) ppm. Mass spectrum: M$^+$ at m/e 362 (theory 362).

EXAMPLE 10

7-[2-(3-R-Hydroxy-1-Octenyl)-5-Oxo-3-Phenylcyclopentyl]-5-Heptenoic Acid

A solution of 3.84 ml. of 2.5M phenyl magnesium chloride in 15 ml. of THF was added dropwise to an ice-cooled mixture of 0.62 g. of 7-[2-(3-R-[tetrahydropyran-2-yloxy]-1-octenyl)-5-oxo-3-cyclopenten-1-yl]-5-heptenoic acid and 0.61 g. of cuprous chloride in 20 ml. of THF and stirred under nitrogen at 0° C. for 0.5 hours. The reaction mixture was added to aqueous ammonium chloride solution and extracted with ether. After washing with water and drying over sodium sulfate, the extract was evaporated and the residue chromatographed on silica. Elution with 20% ethyl acetate in hexane afforded 0.26 g. of an oil which was dissolved in 25 ml. of 20% hydrochloric acid in THF at 0° for 10 minutes. The mixture was diluted with water, extracted with ether and the extract washed with water and dried over sodium sulfate. Evaporation of the solvent and silica chromatography of the residue with 30% ethyl acetate in hexane gave 0.13 g. of the title product as an oil, $\lambda_{max}^{film}$ 3.0 (shoulder), 3.45, 5.8, 10.35, 13.2, 14.3 μ. NMR: δ 7.18 (s, 5, aromatic), 6.25 (s, 2, OH), 5.42 (M, 4, olefinic), 4.02 (M, 1, 15—H) ppm. Mass spectrum: M$^+$ at m/e 412.2587 (theory 412.2613).

EXAMPLE 11

7-[2-(3-S-[Tetrahydropyran-2-Yloxy]-1-Octenyl-5-Oxo-3-Vinylcyclopentyl]-5-Heptenoic Acid A solution of 9.0 ml. of 3.35M vinyl magnesium chloride in 40 ml. of tetrahydrofuran was added dropwise to an ice-cooled mixture of 1.0 g. of 7-[2-(3-S-[tetrahydropyran-2-yloxy]-1-octenyl)-5-oxo-3-cyclopenten-1-yl]-5-heptenoic acid and 2.0 g. of cuprous chloride in 40 ml. of tetrahydrofuran with stirring under nitrogen. After stirring for 0.5 hours at 0°, the reaction mixture was added to aqueous ammonium chloride solution and extracted with ether. After washing with water and drying over magnesium sulfate, the extract was evaporated and the residue chromatographed on silica. Elution with 20% ethyl acetate in hexane gave 0.3 g. of the title product as an oil, $\lambda_{max}^{film}$ 3.45, 5.75, 5.85, 6.1, 9.8, 10.25, 11.0 μ.

EXAMPLE 12

7-[2-(3-S-Hydroxy-1-Octenyl)-5-Oxo-3-Vinylcyclopentyl]-5-Heptenoic Acid

An ice-cooled solution of 0.30 g. of 7-[2-(3-S-[tetrahydropyran-2-yloxy]-octenyl)-5-oxo-3-vinylcyclopentyl]-5-heptenoic acid in 20 ml. of THF was treated with 5.0 ml. of hydrochloric acid and the mixture stirred at 0° for 5 minutes. The reaction mixture was diluted with water, extracted with ether and the extract washed with water and dried over magnesium sulfate. Evaporation and silica chromatography of the residue with 30% ethyl acetate in hexane gave 0.10 g. of the title product as an oil, $\lambda_{max}^{film}$ 3.0, 3.45, 5.8, 6.1, 10.35, 11.0 μ. NMR: δ 4.5–5.8 (M, 7, olefinic H), 4.08 (M, 1, 15—H) ppm. Mass spectrum: M+—H$_2$O at m/e 344.2342 (theory 344.2350).

EXAMPLE 13

7-[2-(3-S-Hydroxy-1-Octenyl)-3-Nitromethyl-5-Oxocyclopentyl]-5-Heptenoic Acid A solution of 0.70 g. of PGA$_2$ and 2.26 ml. of nitromethane in 25 ml. of dry methanol was treated with 0.303 g. of sodium methylate and stirred at 25° under nitrogen for 2 hours. The reaction mixture was added to water, acidifed with acetic acid and extracted with ether. After washing with water and drying over sodium sulfate, the extract was evaporated and the residue chromatographed on silica. Elution with 50% ethyl acetate-hexane gave 0.61 g. of the title product as an oil, $\lambda_{max}^{film}$ 3.0 (shoulder), 3.4, 5.75, 5.85, 6.45, 10.3 μ. NMR: δ 6.42 (s, 2, OH), 5.60 (M, 2, 13 and 14—H), 5.40 (M, 2, 5 and 6—H), 4.47 (M, 2, CH$_2$NO$_2$), 4.15 (M, 1, 15—H) ppm. Mass spectrum: M+—H$_2$O at m/e 377.2225 (theory 377.2201).

EXAMPLE 14

7-[2-(3-S-Hydroxy-1-Octenyl)-3-Methyl-5-Oxocyclopentyl]-5-Heptenoic Acid

A solution of 0.515 g. of PGA$_2$ in 20 ml. of THF was added dropwise over 20 minutes to an ice-cooled stirring mixture of 7.5 ml. of 3M MeMgBr-ether and 1.58 g. of CuCl in 25 ml. of THF under nitrogen. The mixture was stirred at 0° for 15 minutes and at 25° for 15 minutes. The reaction mixture was diluted with aqueous ammonium chloride solution, acidified with acetic acid and extracted with ether. After washing with water and drying over sodium sulfate, the extract was evaporated and the residue chromatographed on silica. Elution with 40% ethyl acetate in hexane gave 0.311 g. of the title product as an oil (solidified on standing, m.p. 63°–68°), $\lambda_{max}^{KBr}$ 3.0, 3.5, 5.8, 8.5, 10.25 μ. NMR: δ 6.57 (s, 2, OH), 5.45 (M, 4, olefinic), 4.15 (M, 1, 15—H) ppm. Mass spectrum: M+ at m/e 350.2556 (theory 350.2456).

EXAMPLE 15

7-[2-(3-S-Hydroxy-1-Octenyl)-5-Oxo-3-Phenylcyclopentyl]-5-Heptenoic Acid

A solution of 5.2 ml. of 2.5M phenyl magnesium bromide in 15 ml. of THF was added dropwise over 15 minutes to an ice-cooled stirring mixture of 0.60 g. of PGA$_2$ and 0.92 g. of cuprous chloride and the mixture stirred at 0° under nitrogen for 1 hour. The reaction mixture was added to aqueous ammonium chloride solution and extracted with ether. After washing with water and drying over sodium sulfate, the extract was evaporated and the residue chromatographed on silica. Elution with 30% ethyl acetate in hexane afforded 0.13 g. of the title product as an oil, $\lambda_{max}^{film}$ 3.0 (shoulder), 3.45, 5.8, 10.3, 13.3, 14.3 μ. NMR: δ 7.22 (s, 5, aromatic), 5.42 (M, 4, olefinic), 4.02 (M, 1, 15—H) ppm. Mass spectrum: M+—H$_2$O at 394.2496 (theory 394.2507).

EXAMPLE 16

7-[3-Benzyl-2-(3-S-Hydroxy-1-Octenyl)-5-Oxocyclopentyl]-5-Heptenoic Acid

An ice-cooled mixture of 1.14 g. of PGA$_2$ and 1.75 g. of cuprous chloride in 50 ml. THF was treated with 10.3 ml. of 2.4M benzyl magnesium chloride in THF and the mixture stirred at 0° for 1 hour under nitrogen. The reaction mixture was added to aqueous ammonium chloride solution, acidified with acetic acid and extracted with ether. After washing with water and drying over sodium sulfate, and extract was evaporated and the residue chromatographed on silica. Elution with 30% ethyl acetate in hexane gave 0.35 g. of the title product as an oil, $\lambda_{max}^{film}$ 3.0 (shoulder), 3.45, 5.8, 6.2, 10.3, 13.3, 14.2 μ. NMR: δ 7.26 (s, 5, aromatic), 5.98 (s, 2, OH), 5.62 (M, 2, 13 and 14—H), 5.42 (M, 2, 5 and 6—H), 4.17 (M, 1, 15—H), 2.29 (d, J=6, benzylic protons) ppm. Mass spectrum: M+ at m/e 426.2749 (theory 426.2768).

EXAMPLE 17

7-[3-Cyano-2-(3-S-Hydroxy-1-Octenyl)-5-Oxocyclopentyl]-5-Heptenoic Acid, Methyl Ester, Acetate A solution of 15.0 g. of 7-[2-(3-S-hydroxy-1-octenyl)-5-oxo-3-cyclopenten-1-yl]-5-heptenoic acid, methyl ester, acetate 3.4 g. of potassium cyanide and 1.9 g. of ammonium chloride in 500 ml. of dimethyl formamide and 100 ml. of water was stirred at 90°–100° C. under nitrogen for 1 hour. After cooling, the mixture was diluted with water, extracted with ether and the extract washed with water and dried over sodium sulfate. Evaporation of the solvent gave 15.5 g. of the title product as an oil, $\lambda_{max}^{film}$ 3.45, 5.75, 7.3, 8.05, 9.85, 10.3 μ.

EXAMPLE 18

7-[3-Cyano-2-(3-S-[Tetrahydropyran-2-Yloxy]-1-Octenyl)-5-Oxocyclopentyl]-5-Heptenoic Acid, Methyl Ester A solution of 0.51 g. of 7-[2-(3-S-[tetrahydropyran-2-yloxy]-1-octenyl)-5-oxo-3-cyclopenten-1-yl-5-heptenoic acid, methyl ester 0.115 g. of potassium cyanide and 0.081 g. of ammonium chloride in 25 ml. of dimethyl formamide and 5 ml. of water was stirred under nitrogen at 90°–100° C. for 1 hour. After cooling to 25°, the mixture was added to water and extracted with ether. After washing with water and drying over sodium sulfate, the extract was evaporated and the residue chromatographed on silica. Elution with 50% ethyl acetate in hexane gave 0.237 g. of the title product as an oil, $\lambda_{max}^{film}$ 3.4, 4.45, 5.7, 8.6, 9175, 10.2, 11.5 μ. NMR: δ 5.1–5.9 (M, 4, olefinic), 4.70 (M, 1, O—CH—O), 3.80 (s, 3, OCH$_3$) ppm. Mass spectrum: M+ at m/e 459 (theory 459), M+—OPy at m/e 358.2423 (theory 358.2381).

EXAMPLE 19

7-[3-Cyano-2-(3-S-Hydroxy-1-Octenyl)-5-Oxocyclopentyl]-5-Heptenoic Acid

An ice-cooled solution of 0.57 g. of 7-[3-cyano-2-(3-S-[tetrahydropyran-2-yloxy]-1-octenyl)-5-oxocyclopentyl]-5-heptenoic acid, methyl ester in 40 ml. THF was treated with 10 ml. of hydrochloric acid and the mixture stirred at 0° for 10 minutes. The reaction mixture was added to water, extracted with ether and the extract washed with water and dried over sodium sulfate. Evaporation of the solvent gave an oil which was dissolved in 50 ml. of 0.5N sodium hydroxide in aqueous methanol and kept at 25° for 0.5 hours. The solution was diluted with water, acidified with hydrochloric acid and extracted with ether. After washing with water and drying over sodium sulfate, the extract was evaporated and the residue chromatographed on silica. Elution with 50% ethyl acetate in hexane gave 0.172 g. of the title product as an oil, $\lambda_{max}^{film}$ 3.0 (shoulder), 3.45, 4.45, 5.75, 7.1, 8.1, 10.3 μ. NMR: δ 6.50 (s, 2, OH), 5.82 (M, 2, 13 and 14—H), 5.42 (M, 2, 5 and 6—H), 4.28 (M, 1, 15—H) ppm. Mass spectrum: $M^+$ at m/e 361 (theory 361).

EXAMPLE 20

7-[2-(3-S-Hydroxy-1-Octenyl)-3-Mercapto-5-Oxo-Cyclopentyl]-5-Heptenoic Acid

A solution of 1.12 g. of $PGA_2$ in 8 ml. of dry tetrahydrofuran was treated at 0° C. with 1.5 g. of sodium sulfide in 6 ml. of water and stirred at 0° C. under nitrogen for one hour. The reaction mixture was added to water, acidified with acetic acid and extracted with ether. After washing with water and drying with magnesium sulfate, the extract was evaporated and the residue chromatographed on silica. Elution with 25% ethyl acetate in hexane gave 0.42 g. of the title product as an oil, $\lambda_{max}^{film}$ 3.00 (shoulder), 3.40, 4.00 (shoulder), 5.70, 5.85, 7.10, 8.10, 10.3 μ. NMR: δ 4.30 (M, 1, 15—H), 5.50 (M, 2, 5 and 6—H), 5.75 (M, 2, 13 and 14—H), 7.15 (s, 2,—OH) ppm. Mass spectrum: $M^+$ at m/e 368.1960 (theory 368.2020).

EXAMPLE 21

7-[3-Ethylthiol-2-(3-S-Hydroxy-1-Octenyl)-5-Oxo-Cyclopentyl]-5-Heptenoic Acid

A solution of 0.5 g. of $PGA_2$ in 2 ml. of ethanethiol was treated with 0.1 ml. of piperidine and stirred at 25° C. for 20 hours. All the solvent was removed in vacuum to give 0.61 g. of the title product as an oil, $\lambda_{max}^{film}$ 3.00 (shoulder), 3.50, 5.75, 5.85, 7.20, 8.10, 10.40 μ. NMR: δ 4.20 (M, 1 15—H), 5.42 (M, 2, 5 and 6—H), 5.70 (M, 2, 13 and 14—H), 6.76 (s, 2, —OH) ppm. Mass spectrum: $M^+$ at m/e 396 (theory 396), $M^+$—$H_2O$ at m/e 378.2241 (theory 378.2228).

EXAMPLE 22

7-[2(3-S-Hydroxy-1-Octenyl)-5-Oxo-3-(Phenylthio)-Cyclopentyl]-5-Heptenoic Acid

A solution of 0.5 g. of $PGA_2$ and 0.2 g. of thiophenol in 6 ml. of dry benzene was treated with 0.1 ml. of piperidine and stirred at 25° C. under nitrogen for 20 hours. The reaction mixture was evaporated and the residue was dissolved with ether.
After washing with water and drying over magnesium sulfate, the ether solution was evaporated and the residue chromatographed on silica. Elution with 30% ethyl acetate in hexane gave 0.62 g. of the title product as an oil, $\lambda_{max}^{film}$ 3.00 (shoulder), 3.50, 5.75, 5.85, 6.30, 10.40, 13.40, 14.50 μ. NMR: δ 4.12 (M, 1, 15—H), 5.39 (M, 2, 5 and 6—H), 5.65 (M, 2, 13 and 14—H), 6.00 (S, 2 —OH), 7.35 (M, 5, aromatic—H) ppm. Mass spectrum $M^+$ at m/e 444.2334 (theory 444.2381).

EXAMPLE 23

3-(6-Carboxy-2-Hexenyl)-α-Cyano-2-(3-S-Hydroxy-1-Octenyl)-4-Oxo-Cyclopentane Acetic Acid Ethyl Ester A solution of 0.58 g. of $PGA_2$ and 0.185 ml. of ethyl cyano acetate in 25 ml. of dimethylformamide was treated with 0.167 g. of 50% sodium hydride-oil dispersion and the mixture stirred under nitrogen at 25° for 0.5 hours. The mixture was diluted with water, acidified with acetic acid and extracted with ether. After washing with water and drying over sodium sulfate, the extract was evaporated and the residue chromatographed on silica. Elution with 30% ethyl acetate in hexane gave 0.435 g. of the title product as an oil, $\lambda_{max}^{film}$ 3.0 (shoulder), 3.5, 4.3 and 4.45 (weak shoulder), 5.8, 8.0, 9.7, 10.3 μ. NMR: δ 6.38 (S, 2, OH), 5.70 (M, 2, 13 and 14—H), 5.55 (m, 2, 5 and 6—H), 4.38 and 3.58 (q, J=7.5, $OCH_2$), 1.25 (t, J=7.5, ester $CH_3$) ppm. Mass spectrum: $M^+$ at m/e 447 (theory 447), $M^+$—$H_2O$ at m/e 429. 2529 (theory 429.2514).

EXAMPLE 24

3-(6-Carboxy-2-Hexenyl)-α-Cyano-2-(3-S-Hydroxy-1-Octenyl)-4-Oxocyclopentane Acetic Acid A solution of 1.424 g. of 3-(6-carboxy-2-hexenyl)-α-cyano-2-(3-S-hydroxy-1-octenyl)-4-oxocyclopentane acetic acid ethyl ester in 100 ml. of 0.5N sodium hydroxide in aqueous methanol was stirred at 25° for 1 hour. The solution was diluted with water, acidified with hydrochloric acid to pH 1 and extracted with ether. After washing with water and drying over sodium sulfate, the extract was evaporated to obtain 1.19 g. of the title product as an oil, $\lambda_{max}^{film}$ 3.4, 4.3 and 4.45 (weak shoulder), 5.8, 7.1, 8.3, 10.3 μ. NMR: δ 7.45 S, 3, OH), 5.70 (M, 2, 13 and 14—H), 5.48 (M, 2, 5 and 6—H), 4.25 (M, 1, 15—H), 3.95 (d, J=6, NC—CH—CO) ppm. Mass spectrum: $M^+$ —$CO_2$ at m/e 375 (theory 375), $M^+$—$CO_2$—$H_2O$ at m/e 356.2217 (theory 356.2225).

EXAMPLE 25

[3-(6-Carboxy-2-Hexenyl)-2-(3-S-Hydroxy-1-Octenyl)-4-Oxocyclopentyl]Malonic Acid 1,3-Diethyl Ester A solution of 1.126 g. of $PGA_2$ and 0.51 ml. of diethyl malonate in 50 ml. of dimethyl acetamide was treated with 0.334 g. of 50% sodium hydride-oil dispersion and the mixture stirred at 25° for 0.5 hours under nitrogen. After diluting with water and acidifying with acetic acid, the mixture was extracted with ether and the extract washed with water and dried over sodium sulfate. Evaporation of the solvent and silica chromatography of the residue with 40% ethyl acetate in hexane gave 0.36 g. of the title product as an oil, $\lambda_{max}^{film}$ 3.0 (shoulder), 3.5, 5.85, 8.7, 9.7, 10.4 μ. NMR: δ 5.3–5.7 (M, 4, olefinic), 4.22 (q, J=7.5, $OCH_2$), 3.55 (M, 1, CO—CH—CO), 1.25 (t, J=7.5, ester $CH_3$) ppm. Mass spectrum: $M^+$ at m/e 494 (theory 494), $M^+$—$H_2O$ at m/e 476.2773 (theory 476.2773).

EXAMPLE 26

[3-(6-Carboxy-2-Hexenyl)-2-(3-S-Hydroxy-1-Octenyl)-4-Oxocyclopentyl] Malonic Acid A solution of 0.28 g. of [3-(6-carboxy-2-hexenyl)-2-(3-S-hydroxy-1-octenyl)-4-oxocyclopentyl]malonic acid 1,3-diethyl ester in 50 ml. of 0.5N sodium hydroxide in aqueous methanol was stirred at 25° for 16 hours. The solution was diluted with water, acidified with acetic acid to pH 4 and washed with ether. The solution was then acidified with hydrochloric acid to pH 1 and extracted with ether. After washing with water and drying over sodium sulfate, the extract was evaporated to obtain 0.164 g. of the title compound as an oil (solidified on standing), $\lambda_{max}^{film}$ 3.5, 5.9, 7.15, 10.35 μ. NMR: δ 5.3–5.6 (M, 4, olefinic), 3.95 (M, 1, 15—H), 3.52 (M, 1, CO—CH—CO) ppm. Mass spectrum: M$^+$—CO$_2$ at m/e 394 (theory 394), M$^+$—CO$_2$—H$_2$O at m/e 376.2231 (theory 276.2248).

EXAMPLE 27

7-[3-Dicyanomethyl-2-(3-S-Hydroxy-1-Octenyl)-5-Oxocyclopentyl]-5-Heptenoic Acid A solution of 1.0 g. of PGA$_2$ and 0.24 g. of malononitrile in 50 ml. of dimethylformamide was treated with 0.28 g. of 50% sodium hydride-oil dispersion and the mixture stirred under nitrogen at 25° for 0.5 hours. The mixture was diluted with water, acidified with acetic acid and extracted with ether. After washing with water and drying over sodium sulfate, the extract was evaporated and the residue chromatographed on silica. Elution with 35% ethyl acetate in hexane gave 0.8 g. of the title product as an oil, $\lambda_{max}^{film}$ 3.0 (shoulder), 3.5, 4.47, 5.8, 7.12, 8.65, 10.3 μ. NMR: δ 5.78 (M, 2, 13 and 14—H), 5.48 (M, 2, 5 and 6—H), 4.25 (M, 2, 15—H and CN—CH—CN) ppm. Mass spectrum: M$^+$ at m/e 400 (theory 400), M$^+$—H$_2$O at m/e 382.2279 (theory 382.2255).

EXAMPLE 28

7-[3-Cyanocarbamoylmethyl-2-(3-S-Hydroxy-1-Octenyl)-5-Oxocyclopentyl]-5-Heptenoic Acid A solution of 1.2 g. of PGA$_2$ and 0.3 g. of 2-cyanoacetamide in 50 ml. of dimethylformamide was treated with 0.34 g. of 50% sodium hydride-oil dispersion and the mixture stirred under nitrogen at 25° for 0.5 hours.

The mixture was diluted with water, acidified with acetic acid and extracted with ether. After washing with water and drying over sodium sulfate, the extract was evaporated and the residue chromatographed on silica. Elution with ethyl acetate gave 0.58 g. of the title product as an oil, $\lambda_{max}^{film}$ 3.2 (shoulder), 3.5, 5.9, 7.45, 10.35 μ. NMR: δ 7.58 (bs, 1, N—H), 7.12 (bs, 1, N—H), 5.25–5.65 (M, 4, olefinic), 3.95 (M, 2, 15—H) and CN—CH—CO) ppm. Mass spectrum: M$^+$—H$_2$O at m/e 400 (theory 400), M$^+$—H$_2$O—CONH$_2$ at m/e 356.2234 (theory 356.2225).

EXAMPLE 29

7-[3-Cyano-2-(3-R-Hydroxy-1-Octenyl)-5-Oxocyclopentyl]-5-Heptenoic Acid, Methyl Ester, Acetate A solution of 1.06 g. of 15-epi-PGA$_2$, methyl ester, acetate and 0.25 g. of potassium cyanide in 25 ml. of dimethylformamide was treated with a solution of 0.18 g. of ammonium chloride in 7.0 ml. of water and the mixture stirred at 100° for 1.5 hours under nitrogen. After cooling, the reaction mixture was added to water, acidified with hydrochloric acid and extracted with ether. After washing with water and drying over sodiium sulfate, the extract was evaporated and the residue chromatographed on alumina (Activity 3). Elution with 20% ethyl acetate in hexane gave 0.77 g. of the title product as an oil, $\lambda_{max}^{film}$ 3.4, 4.5, 5.7, 8.0, 9.75, 10.25 μ. NMR: δ 5.60–5.95 (M, 2, 5 and 6—H), 5.05–5.60 (M, 3, 13, 14 and 15—H), 3.70 (S, 3, OCH$_3$), 2.10 (S, 3, acetate CH$_3$) ppm. Mass spectrum: M$^+$—CH$_3$COOH at m/e 357 (theory 357).

EXAMPLE 30

7-[2-(3-S-Hydroxy-1-Octenyl)-5-Hydroxy-3-Mercapto-Cyclopentyl]-5-Heptenoic Acid A solution of 0.2 g. of 7-[2-(3-S-hydroxy-1-octenyl)-3-mercapto-5-oxo-cyclopentyl]-5-heptenoic acid in 20 ml. of methanol was treated at 0° C with 0.6 g. of sodium borohydride in 10 ml. of methanol and stirred at 0° C for one hour. The reaction mixture was added to water, acidified with acetic acid and extracted with ether. After washing with water and drying with magnesium sulfate, the extract was evaporated and the residue chromatographed on silica. Elution with 30% ethyl acetate in hexane gave 0.09 g. of the title product as an oil, $\lambda_{max}^{film}$ 3.00 (shoulder), 3.40 3.90 (shoulder), 5.85, 7.10, 8.20, 10.30 μ. NMR: δ 4.22 (M, 2, 9 and 15—H), 5.02 (S, 2, —OH), 5.53 (M, 4, olefinic —H) ppm. Mass spectrum: M$^+$ at m/e 370 (theory 370), M$^+$—H$_2$O at m/e 352.2139 (theory 352.2071).

EXAMPLE 31

3-Carbamoyl-2-(3-S-Hydroxyoctanyl)-5-Oxocyclopentyl Heptanoic Acid

A solution of 0.565 g. of 7-[3-carbamoyl-2-(3-S-hydroxy-1-octenyl)-5-oxocyclopentyl]-5-heptenoic acid in 30 ml. of ethyl acetate was added to a prehydrogenated mixture of 0.06 g. of 10% palladium on carbon in 30 ml. of ethyl acetate and the mixture hydrogenated at 25° and atmospheric pressure until 2 equivalents of hydrogen were absorbed. After filtering the catalyst, the solution was evaporated and the residue chromatographed on silica. Elution with ethyl acetate gave 0.075 g. of the title product as an oil, $\lambda_{max}^{film}$ 3.0, 3.5, 6.0, 7.0, 9.6 μ. Mass spectrum: M$^+$ at m/e 383 (theory 383), M$^+$—H$_2$O at m/e 365.2589 (theory 365.2566).

EXAMPLE 32

3-Methyl-2-(3-S-Hydroxyoctyl)-5-Oxocyclopentyl Heptanoic Acid

A solution of 0.222 g. of 7-[3-methyl-2-(3-S-hydroxy-1-octenyl)-5-oxocyclopentyl]-5-heptenoic acid in 20 ml. of ethyl acetate was added to a prehydrogenated mixture of 0.045 g. of 10% palladium on carbon in 20 ml. of ethyl acetate and the mixture hydrogenated at 25° and atmospheric pressure until 2 equivalents of hydrogen were absorbed. After filtering the catalyst, the solution was evaporated and the residue chromatographed on silica. Elution with 25% ethyl acetate in hexane gave 0.085 g. of the title compound as an oil (solidified on standing), $\lambda_{max}^{film}$ 3.0, 3.5, 5.8, 6.85, 8.5 μ. NMR: δ 6.12 (M, OH), 3.68 (M, 15—H), 1.12 (d, J=5.3, 11—CH$_3$) ppm. Mass spectrum: M$^+$ at m/e 354.2807 (theory 354.2768).

EXAMPLE 33

3-Carboxy-2-(3-S-Hydroxyoctyl)-5-Oxocyclopentyl Heptanoic Acid

A solution of 0.26 g. of 7-[3-carboxy-2-(3-S-hydroxy-1-octenyl)-5-oxocyclopentyl]-5-heptenoic acid in 20 ml. of ethyl acetate was added to a prehydrogenated mixture of 0.05 g. of 10% palladium on carbon in 20 ml. of ethyl acetate and hydrogenated at 25° and atmospheric pressure until 2 equivalents of hydrogen were absorbed. After filtering the catalyst, the solution was evaporated and the residue chromatographed on silica. Elution with 40% ethyl acetate in hexane gave 0.09 g. of the title compound as an oil, $\lambda_{max}^{film}$ 3.0 (shoulder), 3.45, 5.8, 7.1 μ. NMR: δ 7.88 and 7.68 (M, OH) 3.68 (M, 15—H) ppm. Mass spectrum: M+ at m/e 284 (theory 284), M+—H$_2$O at m/e 366.2368 (theory 366.2405).

EXAMPLE 34

3-Benzyl-2-(3-S-Hydroxyoctyl)-5-Oxocyclopentyl Heptanoic Acid

A solution of 0.175 g. of 7-[3-benzyl-2-(3-S-hydroxy-1-octenyl)-5-oxocyclopentyl]-5-heptenoic acid in 15 ml. of ethyl acetate was added to a prehydrogenated mixture of 0.035 g. of 10% palladium on carbon in 15 ml. of ethyl acetate and the mixture hydrogenated at 25° and atmospheric pressure until 2 equivalents of hydrogen were absorbed. After filtering the catalyst, the solution was evaporated and the residue chromatographed on silica. Elution with 30% ethyl acetate gave 0.082 g. of the title compound as an oil, $\lambda_{max}^{film}$ 3.0 (shoulder), 3.5, 5.8, 6.23, 6.67, 6.88, 13.4, 14.34 μ. NMR: δ 7.30 (S, aromatic —H), 6.42 (S, OH), 3.65 (M, 15—H) ppm. Mass spectrum: M+ at m/e 430.3098 (theory 430.3082).

EXAMPLE 35

7-[8-Cyano-7-(3-S-Hydroxy-1-Octenyl)-1,4-Dioxaspiro[4,4] Non-6-Yl]-5-Heptenoic Acid, Methyl Ester, Acetate A solution of 15.3 g. of 7-[3-cyano-2-(3-S-hydroxy-1-octenyl)-5-oxocyclopentyl]-5-heptenoic acid, methyl ester, acetate and 0.94 g. of p-toluenesulfonic acid in 920 ml. of benzene and 92 ml. of ethylene glycol was refluxed with a water separator for 24 hours. After cooling, the reaction mixture was diluted with ether, washed with water and dried over sodium sulfate. Evaporation of the solvent and silica chromatography of the residue with 20% ethyl acetate in hexane gave 12.0 g. of the title product as an oil, $\lambda_{max}^{film}$ 3.4, 4.45, 5.73, 8.1, 8,63, 9.7, 10.3 μ.

EXAMPLE 36

7-[8-Cyano-7-(3-S-Hydroxy-1-Octenyl)-1,4-Dioxaspiro [4.4]Non-6-Yl]-5-Heptenoic Acid A solution of 12.0 g. of 7-[8-cyano-7-S-hydroxy-1-octenyl)-1,4-dioxaspiro[4.4]non-6-yl]-5-heptenoic acid, methyl ester, acetate in 330 ml. of methanol and 330 ml. of 1N sodium hydroxide was stirred at 25° for 1 hour. The reaction mixture was diluted with water, acidified with acetic acic and extracted with ether. After washing with water and drying over sodium sulfate, the extract was evaporated and the residue chromatographed on silica. Elution with 33% ethyl acetate in hexane gave 9.4 g. of the title product as an oil, $\lambda_{max}^{film}$ 3.0 (shoulder), 3.45, 4.45, 5.8, 8.65, 9.65, 10.3 μ. NMR: δ 7.1 (S, 2, OH), 5.70 (M, 2, 13 and 14—H), 5.40 (M, 2, 5 and 6—H), 4.15 (M, 1, 15—H), 3.92 (S, 4, ketal H) ppm. Mass spectrum: M+ at m/e 405.2582 (theory 405.2514).

EXAMPLE 37

7-[8-Carboxy-7-(3-S-Hydroxy-1-Octenyl)-1,4-Dioxaspiro[4.4]Non-6-YL]-5-Heptenoic Acid and 7-[8-Carboxy-7-(3-S-Hydroxy-1-Octenyl-1,4-Dioxaspiro[4.4]Non-6-YL]-5-Heptenoic Acid A solution of 0.28 g. of 7-[8-cyano-7-(3-S-hydroxy-1-octenyl)-1,4-dioxaspiro[4.4]non-6-yl]-5-heptenoic acid in 60 ml. of 0.5N sodium hydroxide in aqueous methanol was refluxed under nitrogen for 5 hours. The mixture was cooled, diluted with water, acidified with acetic acid and extracted with ether. After washing with water and drying over sodium sulfate, the extract was evaporated and the residue chromatographed on silica. Elution with 50% ethyl acetate in hexane gave 0.115 g. of first title product as an oil, $\lambda_{max}^{film}$ 3.0 (shoulder), 3.45, 5.85, 8.7, 9.65, 10.3 μ. NMR: δ 5.68 (M, 4, olefinic), 4.12 (M, 15—H), 3.98 (S, 4, ketal) ppm. Mass spectrum: M+ at m/e 424.2462 (theory 424.2460).

Further elution with 1:2:97 acetic acid:methanol:ethyl acetate afforded 0.10 g. of the second title product as an oil (solidified on standing), $\lambda_{max}^{film}$ 3.0 (shoulder), 3.45, 5.8, 8.7, 9.6, 10.3 μ. NMR: 6.4–7.3 (M, 4, OH and NH), 5.60 (M, 4, olefinic), 4.05 (M, 5, 15—H and ketal H) ppm. Mass spectrum: M+ at m/e 423.2674 (theory 423.2620).

EXAMPLE 38

7-[8-Formyl-7-(3-S-Hydroxy-1-Octenyl)-1,4-Dioxaspiro[4,4]Non-6-Yl]-5-Heptenoic Acid A solution of 0.405 g. of 7-[8-cyano-7-(3-S-hydroxy-1-octenyl)-1,4-dioxaspiro[4.4]non-6-yl]-5-heptenoic acid and 0.096 g. of 50% sodium hydride-oil dispersion in 10 ml. of THF was added to a mixture of 5.0 ml. of 1M lithium aluminum hydride and 0.73 ml. of ethyl acetate in 1.70 ml. of THF and stirred under nitrogen at 25° for 1 hour. The reaction mixture was treated with 5 ml. of methanol, diluted with water, acidified with acetic acid and extracted with ether. After washing with water and drying over sodium sulfate, the extract was evaporated to obtain 0.35 g. of the title product as an oil, $\lambda_{max}^{film}$ 3.0, 3.45, 5.8, 8.7, 9.7, 10.3 μ. NMR: δ 9.50 (M, aldehyde H), 5.62 (M, 2, 13 and 14—H), 5.42 (M, 2, 5 and 6—H), 4.10 (M, 1, 15—H), 3.92 (S, 4, ketal H) ppm.

EXAMPLE 39

7-[8-Hydroxymethyl-7-(3-S-Hydroxy-1-Octenyl-1,4-Dioxaspiro[4.4]Non-6-Yl]-5-Heptenoic Acid A solution of 0.25 g. of 7-[8-formyl-7-[3-S-hydroxy-1-octenyl)-1,4-dioxaspiro[4.4]non-6-yl]-5-heptenoic acid in 20 ml. of methanol was treated with a solution of 0.90 g. of sodium borohydride in 70 ml. of methanol and the mixture stirred at 25° for 1 hour. After concentrating the mixture under 40° under vacuum, the residue was diluted with water, washed with ether, acidified with acetic acid and extracted with ether. After washing with water and drying over sodium sulfate, the ether extract was evaporated to give 0.125 g. of the title product as an oil, $\lambda_{max}^{film}$ 3.25 (shoulder), 3.5, 5.9, 7.2, 8.2 μ. Mass spectrum: M+ m/e 410.2724 (theory 410.2666).

EXAMPLE 40

7-[8-Acetyl-7-(3-S-Hydroxy-1-Octenyl)-1,4-Dioxaspiro[4.4]Non-6-Yl]-5-Heptenoic Acid A solution of 0.623 g. of 7-[8-cyano-7-(3-S-hydroxy-1-octenyl)-1,4-dioxaspiro[4.4]non-6-yl]-5-heptenoic acid in 35 ml. of THF was treated with 2.54 ml. of 3M methyl magnesium bromide in ether and the mixture refluxed under nitrogen for 1 hour. After cooling, the mixture was diluted with water, acidified with acetic acid and extracted with ether. After evaporation of the ether, the residue was redissolved in 10 ml. of THF and 100 ml. of 0.5N sodium hydroxide. The solution was washed with ether, acidified with acetic acid and extracted with ether. After washing with water and drying over sodium sulfate, the extract was evaporated and the residue chromatographed on silica. Elution with 40% ethyl acetate in hexane gave 0.10 g. of the title product as an oil, $\lambda_{max}^{film}$ 3.0, 3.4, 5.75, 8.55, 9.5 $\mu$. NMR: $\delta$ 5.88 (M, 2, OH), 5.68 (M, 2, 13 and 14—H), 5.42 (M, 2, 5 and 6—H), 4.10 (M, 1, 15—H), 3.95 (S, 4, ketal), 2.15 (S, COCH$_3$) ppm. Mass spectrum: M$^+$ at m/e 422.2658 (theory 422.2666).

EXAMPLE 41

7-[8-(1-Hydroxyethyl)-7-(3-S-Hydroxy-1-Octenyl)-1,4-Dioxaspiro[4.4]Non-6-Yl]-5-Heptenoic Acid An ice-cooled solution of 0.63 g. of 7-[8-acetyl-7-3-S-hydroxy-1-octenyl)-1,4-dioxaspiro[4.4]non-6-yl]-5-heptenoic acid in 40 ml. of methanol was treated with a cold solution of 1.87 g. of sodium borohydride in 150 ml. of methanol and the mixture stirred at 25° for 1 hour. After concentrating the mixture at 40° in vacuo, the residue was diluted with water, acidified with acetic acid and extracted with ether. After washing with water and drying over sodium sulfate, the extract was evaporated and the residue chromatographed on silica. Elution with 60% ethyl acetate in hexane gave 0.46 g. of the title product as an oil, $\lambda_{max}^{film}$ 3.2, 3.5, 5.9, 9.7, 10.35 $\mu$. Mass spectrum: M$^+$ at m/e 424 (theory 424).

EXAMPLE 42

7-[8-Nitromethyl-7-(3-R-Hydroxy-1-Octenyl)-1,4-Dioxaspiro[4.4]Non-6-Yl]-5-Heptenoic Acid, Methyl Ester, Acetate A solution of 1.0 g. of 7-[2-(3-R-hydroxy-1-octenyl)-3-nitromethyl-5-oxocyclopentyl]-5-heptenoic acid, methyl ester, acetate and 0.125 g. of p-toluenesulfonic acid in 125 ml. of benzene and 12.0 ml. of ethylene glycol was refluxed with a water separator for 20 hours. After cooling, the mixture was diluted with ether, washed with water and dried over sodium sulfate. Evaporation of the solvent and silica chromatography of the residue with 30% ethyl acetate in hexane gave 0.685 g. of the title product as an oil, $\lambda_{max}^{film}$ 3.45, 5.8, 6.5, 7.0, 7.35, 8.15, 9.9, 10.35 $\mu$. NMR: $\delta$ 5.0-5.6 (M, 5, olefinic and 15—H), 4.28 (m 2, CH$_2$NO$_2$), 3.90 (S, 4, ketal), 3.68 (S, 3, OCH$_3$), 2.02 (S, COCH$_3$) ppm. Mass spectrum: M$^+$ at m/e 495 (theory 495), M$^+$-CH$_3$COOH at m/e 435.2636 (theory 435.2620).

EXAMPLE 43

7-[8-Nitromethyl-7-(3-R-Hydroxy-1-Octenyl)-1,4-Dioxaspiro[4.4]Non-6-Yl]-5-Heptenoic Acid A solution of 4.5 g. of 7-[8-nitromethyl-7-(3-R-hydroxy-1-octenyl)-1,4-dioxaspiro[4.4]non-6-yl]-5-heptenoic acid, methyl ester, acetate in 150 ml. of methanol and 120 ml. of 1N sodium hydroxide was stirred under nitrogen at 25° for 1 hour. The solution was diluted with water, acidified with acetic acid and extracted with ether. After washing with water and drying over sodium sulfate, the extract was evaporated and the residue chromatographed on silica. Elution with 30% ethyl acetate in hexane gave 3.68 g. of the title product as an oil (solidified on standing), $\lambda_{max}^{KBr}$ 3.0, 3.45, 5.85, 6.45, 6.9, 7.95, 9.15, 10.25 $\mu$. NMR: $\delta$ 6.55 (S, 2, OH), 5.62 (M, 4, olefinic), 4.30 (M, 3, 15—H and CH$_2$NO$_2$), 3.92 (S, 4, ketal) ppm. Mass spectrum: M$^+$ at m/e 439 (theory 439), M$^+$-NO$_2$ at m/e 393.2651 (theory 393.2639).

EXAMPLE 44

7-[8$\alpha$-Cyano-7-(3-R-Hydroxy-1-Octenyl)-1,4-Dioxaspiro[4.4]Non-6-Yl]-5-Heptenoic Acid, Methyl Ester, Acetate and 7-[8$\beta$-Cyano-7-(3-R-Hydroxy-1-Octenyl)-1,4-Dioxaspiro[4.4]Non-6-Yl]-5-Heptenoic Acid, Methyl Ester, Acetate A solution of 3.4 g. of 7-[3-cyano-2-(3-R-hydroxy-1-octenyl)-5-oxocyclopentyl]-5-heptenoic acid, methyl ester, acetate and 0.15 g. of p-toluenesulfonic acid in 150 ml. of benzene and 15 ml. of ethylene glycol was refluxed with a water separator for 22 hours. After cooling, the reaction mixture was diluted with ether, washed with water and dried over sodium sulfate. Evaportion of the solvent and silica chromatography of the residue with 25% ethyl acetate in hexane gave 1.19 g. of the first title product as an oil, $\lambda_{max}^{film}$ 3.45, 4.5, 5.75, 8.1, 9.8, 10.3 $\mu$. NMR: $\delta$ 5.5-5.7 (M, 2, 5 and 6—H), 5.0-5.5 (M, 3, 13, 14 and 15—H), 3.93 (S, 4, ketal), 3.68 (S, 3, OCH$_3$), 2.03 (S, acetate CH$_3$) ppm. Mass spectrum: M$^+$ at m/e 461 (theory 461), M$^+$—HC$_2$H$_3$O$_2$ at m/e 401.2557 (theory 401.2565).

Further elution with 25% ethyl acetate in hexane afforded 0.93 g. of the second title product as an oil, $\lambda_{max}^{film}$ 3.45, 4.5, 5.75, 8.1, 9.8, 10.3 $\mu$. NMR: $\delta$ 5.55-5.95 (M, 2, 5 and 6—H), 5.05-5.55 (M, 3, 13, 14 and 15—H), 3.92 (S, 4, ketal), 3.68 (S, 3, OCH$_3$), 3.07 (q, J=7.5, 11—H), 2.05 (S, acetate CH$_3$) ppm. Mass spectrum: M$^{30}$ at m/e 461 (theory 461), M$^+$—HC$_2$H$_3$O$_2$ at m/e 401.2532 (theory 401.2565).

EXAMPLE 45

7-[8A-Cyano-7-(3-R-Hydroxy-1-Octenyl)-1,4-Dioxaspiro[4.4]Non-6-Yl]-5-Heptenoic Acid (A) A solution of 1.10 g. of 7-[8a-cyano-7-(3-R-hydroxy-1-octenyl)-1,4-dioxaspiro[4.4]non-6-yl]-5-heptenoic acid, methyl ester, acetate in 25 ml. of methanol was treated with 25 ml. of 1N sodium hydroxide and the mixture stirred at 25° under nitrogen for 1 hour. The mixture was diluted with water, acidified with acetic acid and extracted with ether. After washing with water and drying over sodium sulfate, the extract was evaporated and the residue chromatographed on silica. Elution with 30% ethyl acetate in hexane followed by crystallization from ethyl acetate and pentane afforded 0.37 g. of the title product, m.p. 88.5°-89.5°, mixed m.p. with the 8$\beta$ isomer 75°-80°, $\lambda_{max}^{KBR}$ 3.15, 3.45, 4.0, 5.85, 7.2, 8.1, 8.7, 9.6, 10.4, 11.0, 14.2 $\mu$. NMR: 7.35 (S, 2, OH), 5.1-5.9 (M, 4, olefinic H), 4.12 (M, 1, 15—H), 3.95 (S, 4, ketal H) ppm. Mass spectrum: M$^+$ at m/e 405 (theory 405), M$^+$—H$_2$O at m/e 387.2379 (theory 387.2409).

(B) A solution of 0.20 g. of 7-[8$\beta$-cyano-7-(3-R-hydroxy-1-octenyl)-1,4-dioxaspiro[4.4]non-6-yl]-5-heptenoic acid in 20 ml. of tertiary butyl alcohol was treated with 0.28 g. of potassium tertiary butoxide and the mixture stirred at 25° under nitrogen for 16 hours. Following dilution with water and acidification with acetic acid, the mixture was extracted with ether and the extract washed with water and dried over sodium sulfate. Evaportion of the solvent and silica chromatography with 50% ethyl acetate in hexane gave 0.16 g. of the title product as white crystals. A recrystallized sample (ethyl acetate-pentane) exhibited m.p. 84°–86°, mixed m.p. with authentic 8α-isomer 87°–89° and mixed m.p. with 8β-isomer 73°–76°.

EXAMPLE 46

7-[8β-Cyano-7-(3-R-HYdroxy-1-Octenyl)-1,4-Dioxaspiro[4.4]Non-6-Yl]-5-Heptenoic Acid A solution of 0.83 g. of 7-[8β-cyano-7-(3-R-hydroxy-1-octenyl)-1,4-dioxaspiro[4.4]non-6-yl]-5-heptenoic acid, methyl ester, acetate in 25 ml. of methanol was treated with 25 ml. of 1N sodium hydroxide and the mixture stirred at 25° under nitrogen for 1 hour. The solution was diluted with water, acidified with acetic acid and extracted with ether. After washing with water and drying over sodium sulfate, the extract was evaporated and the residue chromatographed on silica. Elution with 30% ethyl acetate - hexane followed by crystallization from ethyl acetate and pentane afforded 0.23 g. of the title product, m.p. 88°–89°, mixed m.p. with the 8α isomer 75°–80°, $\lambda_{max}^{KBr}$ 3.1, 3.45, 5.95, 7.55, 7.65, 7.85, 8.7, 9.6, 10.35, 11.0, 13.25 μ. NMR: 7.23 (S, 2, OH), 5.70 (M,2, 5 and 6—H), 5.45 (M, 2, 13 and 14—H), 4.20 (M, 1, 15—H), 3.95 (S, 4, ketal H), 3.08 (q, J=7.3, 11—H), ppm. Mass spectrum: M+ at m/e 405 (theory 405), M+—H$_2$O 387.2417 (theory 387–2409)

EXAMPLE 47

7-[3-Carboxy-2-(3-S-Hydroxy-1-Octenyl-5-Oxocyclopenyl]-5-Heptenoic Acid

A solution of 0.70 g. of 7-[8-carboxy-7-(3-S-hydroxy-1-octenyl)-1,4-dioxaspiro[4.4]non-6-yl]-5-heptenoic acid in 50 ml. of THF and 5.0 ml. of hydrochloric acid was stirred at 25° for 0.5 hours. The mixture was diluted with water, extracted with ether and the extract washed with water and dried over sodium sulfate. Evaportion of the solvent and silica chromatography of the residue with 50% ethyl acetate in hexane gave 0.45 g. of the title product as an oil, $\lambda_{max}^{film}$ 3.5, 5.85, 7.15, 8.2, 10.4 μ. NMR: δ 5.68 (M, 2, 13 and 14—H), 5.45 (M, 2, 5 and 6—H), 4.20 (M, 1, 15—H) ppm. Mass spectrum: M+ at m/e 380 (theory 380), M+—H$_2$O at m/e 362.2123 (theory 362.2093).

EXAMPLE 48

7-[3-Carbamoyl-2(3-S-Hydroxy-1-Octenyl)-5-Oxocyclopentyl]-5-Heptenoic Acid

A solution of 0.51 g. of 7-[8-carbamoyl-7-(3-S-hydroxy-1-octenyl)-1,4-dioxaspiro[4.4]non-6-yl]-5-heptenoic acid in 50 ml. of THF and 5.0 ml. of hydrochloric acid was stirred at 25° for 0.5 hours. The mixture was diluted with water, extracted with ether and the extract washed with water and dried over sodium sulfate. Evaporation of the solvent and silica chromatography of the residue with 1:2:97 acetic acid: methanol:ethyl acetate gave 0.38 g. of the title product as an oil, $\lambda_{max}^{film}$ 3.0, 3.4, 5.7, 5.9, 6.1 (shoulder), 8.0, 10.3 μ. NMR: δ 6.4–6.9 (M, 4, OH and NH), 5.65 (M, 2, 13 and 14—H), 5.42 (M, 2, 5 and 6—H), 4.15 (M, 1, 15—H) ppm. Mass spectrum: M+ at m/e 379 (theory 379), M+—2H$_2$O at m/e 343.2155 (theory 343.2146).

EXAMPLE 49

7-[3-Hydroxymethyl-2-(3-S-Hydroxy-1-Octenyl-5-Oxocyclopentyl]-5-Heptenoic Acid

An ice-cooled solution of 0.255 g. of 7-[8-hydroxymethyl-7-(3-S-hydroxy-1-octenyl)-1,4-dioxaspiro[4.4]-non-6-yl]-5-heptenoic acid in 25 ml. of THF was treated with 2.5 ml. of hydrochloric acid and the mixture stirred at 0° for 0.5 hours. The reaction mixture was diluted with ether, washed with water, dried over sodium sulfate and evaporated. Silica chromatography of the residue with 70% ethyl acetate in hexane gave 0.056 g. of the title product as an oil, $\lambda_{max}^{film}$ 3.0, 3.45, 5.8, 7.1, 8.1, 10.3 μ. NMR: δ 5.1–5.8 (M, 7, 4-olefinic H, 3—OH), 4.12 (M, 1, 15—H), 3.72 (M, 2, 0—CH$_2$) ppm. Mass spectrum: M+ at m/e 366 (theory 366), M+—C$_5$H$_{11}$ at m/e 295.1551 (theory 295.1544).

EXAMPLE 50

7-3-Acetyl-2-(3-S-Hydroxy-1-Octenyl)-5-Oxocyclopentyl]-5-Heptenoic Acid

A solution of 0.16 g. of 7-[8-acetyl-7-(3-S-hydroxy-1-octenyl)-1,4-dioxaspiro[4.4]non-6-yl]-5-heptenoic acid in 15 ml. of THF and 1.5 ml. of hydrochloric acid was stirred at 25° for 0.5 hours. The mixture was diluted with water, extracted with ether and the extract washed with water and dried over sodium sulfate. Evaporation and silica chromatography of the residue with 40% ethyl acetate in hexane gave 0.13 g. of the title product as an oil, $\lambda_{max}^{film}$ 3.0, 3.45, 5.8, 7.1, 8.6, 10.3 μ. NMR: δ 6.12 (S, 2, OH), 5.68 (M, 2, 13 and 14—H), 5.42 (M, 2, 5 and 6—H), 4.20 (M, 1, 15—H), 2.20 (S, COCH$_3$) ppm. Mass spectrum: M+ at m/e 378.2438 (theory 378.2405).

EXAMPLE 51

7-[3-(1-Hydroxyethyl)-7-(3-S-Hydroxy-1-Octenyl)-5-Oxocyclopentyl]-5-Heptenoic Acid A solution of 0.46 g. of 7-[8-(1-hydroxyethyl)-7-(3-S-hydroxy-1-octenyl)-1,4-dioxaspiro[4.4]non-6-yl]-5-heptenoic acid in 30 ml. of THF and 3.0 ml. of hydrochloric acid was stirred at 25° for 0.5 hours. The mixture was diluted with water, extracted with ether and the extract washed with water and dried over sodium sulfate. Evaporation of the solvent and silica chromatography of the residue with 50% ethyl acetate in hexane gave 0.14 g. of the title product as an oil, $\lambda_{max}^{film}$ 3.0, 3.5, 5,85, 7.15, 8.2, 10.4 μ. NMR: δ 5.50 (M, 4, olefinic), 4.02 (M, 2, O—CH), 1.20 (d, J=6, Me—CH) ppm. Mass spectrum: M+—H$_2$O at m/e 362 (theory 362), M+—2H$_2$O at m/e 344.2367 (theory 344.2350).

EXAMPLE 52

7-[8-Nitromethyl-7-(3-Oxo-1-Octenyl)-1,4-Dioxaspiro[4.4]Non-6-Yl]-5-Heptenoic Acid A solution of 0.2 g. of 7-[8-nitromethyl-7-(3-R-hydroxy-1-octenyl)-1,4-dioxaspiro[4.4]non-6-yl]-5-heptenoic acid in 5 ml. of acetone was treated at −10° with 0.1 ml. of Jones reagent and stirred at 0° C. for 15 minutes. Following the addition of 1 ml. of methanol, the reaction mixture was basified with aqueous sodium bicarbonate solution, acidified with acetic acid and extracted with ether. After washing with water and drying with magnesium sulfate, the extract was evaporated and the residue chromatographed on silica. Elution with 30% ethyl acetate in hexane gave 0.17 g. of the title product as a semi-solid, $\lambda_{max}^{film}$ 3.50, 5.87, 6.15

(shoulder), 6.45, 7.25 μ. NMR: δ 3.95 (S, 4, ketal), 4.30 (M, 2, —CH$_2$NO$_2$), 5.20–5.80 (M, 3, 5, 6 and 14—H), 6.20–2.90 (M, 1, 13—H), 8.28 (S, 1, OH) ppm. UV λ$_{max}^{EtOH}$ 223 mμ (ε 8,740). Mass spectrum: M$^+$ at m/e 437.2456 (theory 437.2480).

EXAMPLE 53

7-[8a-Cyano-7-(3-Oxo-1-Octenyl)-1,4-Dioxaspiro[4.4]-Non-6-Yl]-5-Heptenoic Acid

A solution of 1.0 g. of 7-[8α-cyano-7-(3-R-hydroxy-1-octenyl)-1,4-dioxaspiro[4.4]non-6-yl]-5-heptenoic acid in 50 ml. of acetone was treated at 0° C. with 3.4 ml. of 1.2M Jones reagent and stirred at 0° C. under nitrogen for 3/4 hours. The reaction mixture was treated with 3 ml. of ethanol and neutralized with aqueous sodium bicarbonate solution. After acidification by acetic acid, the mixture was extracted with ether and the extract washed with brine and dried with magnesium sulfate. The extract was evaporated and the residue chromatographed on silica. Elution with 35% ethyl acetate-hexane gave 0.95 g. of the title product as an oil, λ$_{max}^{film}$ 3.5, 4.5, 5.8 (shoulder), 5.85, 6.10, 8.60, 9.70 μ. UV λ$_{max}^{EtOH}$ 225 mμ (ε 13,000). NMR: δ 3.95 (S, 4, ketal), 5.42 (M, 2, 5 and 6—H), 6.42 (M, 2, 13 and 14—H), 9.65 (M, 1, —OH) ppm. Mass spectrum: M$^+$ at m/e 403.2334 (theory 403.2357).

EXAMPLE 54

7-[8β-Cyano-7-(3-Oxo-1-Octenyl)-1,4-Dioxaspiro [4.4]Non-6-Yl]-5-Heptenoic Acid

A solution of 4.05 g. of 7-[8β-cyano-7-(3-R-hydroxy-1-octenyl)-1,4-dioxaspiro[4.4]non-6-yl]-5-heptenoic acid in 50 ml. of acetone was treated at 0° C. with 3.5 mls. of 1.2 M Jones reagent and stirred at 0° C. for 3/4 hour. The reaction mixture was treated with 3 ml. of ethanol and neutralized with aqueous sodium bicarbonate solution. After acidification with acetic acid, the mixture was extracted with ether and the extract washed with brine and dried with magnesium sulfate. Evaporation of the dried ether extract gave 4.00 g. of the title product as a solid, which was recrystallized from ether-pentane mixture to give white crystals, m.p. 52°–54° C., λ$_{max}^{film}$ 3.45, 4.50, 5.70 (shoulder), 5.85, 6.10, 8.70, 9.70 μ. UV λ$_{max}^{EtOH}$ 225 mμ (ε 11,000). NMR: δ 3.21 (q, J=7.5, 11—H), 4.00 (S, 4, ketal), 5.46 (M, 2, 5 and 6—H), 6.22 (d, J=16, 14—H), 6.98 (dd, J=9, 16, 13—H). Mass spectrum: M$^+$ at m/e 403.2357 (theory 403.2357).

EXAMPLE 55

7-[8-Nitromethyl-7-(3-Methyl-3-Hydroxyl-1-Octenyl)-1,4-Dioxaspiro[4.4]Non-6-Yl]-5-Heptenoic Acid A solution of 1.72 g. of 7-[8-nitromethyl-7-(3-oxo-1-octenyl)-1,4-dioxaspiro[4.4]non-6-yl]-5-heptenoic acid in 80 ml. of tetrahydrofuran was treated at −10° C. with 9.7 ml. of 3M methyl magnesium bromide in tetrahydrofuran and was stirred at 0° C. for one hour. The reaction mixture was added to aqueous ammonium chloride solution, acidified with acetic acid and extracted with ether. After washing with water and drying over magnesium sulfate, the extract was evaporated and the residue chromatographed on silica. Elution with 30% ethyl acetate in hexane gave 0.26 g. of the title product as an oil, λ$_{max}^{film}$ 3.00 (shoulder), 3.45, 5.80 (shoulder), 5.85, 6.45, 7.25, 10.30 μ. NMR: δ 1.32 (S, 15-methyl), 4.01 (S, 4, ketal), 4.40 (M, 2, CH$_2$NO$_2$), 5.22 (M, 2, 5 and 6—H), 5.63 (M, 2, 13 and 14—H) ppm. Mass spectrum: M$^+$ at m/e 453), (theory 453), M$^+$—H$_2$O at m/e 435.2571 (theory 435.2620).

EXAMPLE 56

7-[8-Nitromethyl-7-(3-Hydroxy-3-Phenyl-1-Octenyl)-1,4-Dioxaspiro[4.4]Non-6-Yl]-5-Heptenoic Acid A solution of 1.88 g. of 7-[8-nitromethyl-7-(3-oxo-1-octenyl)-1,4-dioxaspiro[4.4]non-6-yl]-5-heptenoic acid in 80 ml. of tetrahydrofuran was treated at −10° C. with 6.6 ml. of 3M phenyl magnesium bromide in tetrahydrofuran and was stirred at 0° C. for one hour. The reaction mixture was added to aqueous ammonium chloride solution, acidified with acetic acid and extracted with ether. After washing with water and drying with magnesium sulfate, the extract was evaporated and the residue chromatographed on silica. Elution with 30% ethyl acetate in hexane gave 0.90 g. of the title product as an oil, λ$_{max}^{film}$ 3.00 (shoulder), 3.50, 5.88, 6.28, 6.47, 6.95, 7.25, 13.30, 14.35 μ. NMR: δ 3.93 (S, 4, ketal), 4.35 (M, 2, —CH$_2$NO$_2$), 5.15–6.05 (M, 4, olefinic —H), 5.88 (S, 2, —OH), 7.45 (M, 5, aromatic-HO ppm. Mass spectrum: M$^+$ at m/e 515 (theory 515), M$^+$—H$_2$O at m/e 497.2776 (theory 497.2776.

EXAMPLE 57

7-[8α-Cyano-7-(3-Methyl-3-Hydroxy-1-Octenyl)-1,4-Dioxaspiro[4.4]Non-6-Yl]-5-Heptenoic Acid A solution of 0.98 g. of 7-[8α-cyano-7-(3-oxo-1-octenyl)-1,4-dioxaspiro[4.4]non-6-yl]-5-heptenoic acid in 35 ml. of dry tetrahydrofuran was treated under nitrogen at −10° C. with 5 ml. of 3M methyl magnesium bromide in tetrahydrofuran and stirred at −10° C for one and a half hours. The reaction mixture was added to 20 ml. of saturated aqueous ammonium chloride solution, acidified with acetic acid and extracted with ether. After washing with brine and drying with magnesium sulfate, the ether extract was evaporated to give 1.02 g. of the title product as an oil, λ$_{max}^{film}$ 3.0 (shoulder), 3.5, 4.4, 5.8, 8.7, 9.4 μ. NMR: δ 1.32 (S, 15—Ch$_3$), 4.01 (S, 4, ketal), 5.50–5.80 (M, 4, olefinic H), 6.88 (S, 2, —OH) ppm. Mass spectrum: M$^+$ at m/e 419.2679 (theory 419.2671).

EXAMPLE 58

7-[8β-Cyano-7-(3-Hydroxy-3-Methyl-1-Octenyl)-1,4-Dioxaspiro[4.4]Non-6-Yl]-5-Heptenoic Acid A solution of 0.87 g. of 7-[8β-cyano-7-(3-oxo-1-octenyl)-1,4-dioxaspiro[4.4]non-6-yl]-5-heptenoic acid in 35 ml. of THF was treated under nitrogen at 0° C. with 5 ml. of 3M methyl magnesium bromide in THF and stirred at 0° C. for one and a half hours. The reaction mixture was added to 20 ml. of saturated aqueous ammonium chloride solution, acidified with acetic acid and extracted with ether. After washing with brine and drying with magnesium sulfate, the ether extract was evaporated and the residue chromatographed on silica. Elution with 20% ethyl acetatehexane gave 0.54 g. of 7-[8α-cyano-7-(3-hydroxy-3-methyl-1-octenyl)-1,4-dioxaspiro[4.4]non-6-yl]-5-heptenoic acid. Continued elution with 20% ethyl acetate-hexane gave 0.08 g. of the title product as an oil, λ$_{max}^{film}$ 2.95 (shoulder), 3.40, 4.40, 5.80, 8.65, 9.60 μ. NMR: δ 1.30 (S, 15-methyl), 3.10 (q J=7.5, 11—H), 3.92 (S, 4, ketal), 5.40 (M, 2, 5 and 6—H), 5.70 (d, 2, J=4, 13 and 14—H), 6.10 (S, 2, —OH). Mass spectrum: M$^+$ at m/e 419 (theory 419), M$^+$—H$_2$O at m/e 401.2557 (theory 401.2565).

EXAMPLE 59

7-[2-(3-Hydroxy-3-Methyl-1-Octenyl)-3-Nitromethyl-5-Oxocyclopentyl]-5-Heptenoic Acid A solution of 0.20 g. of 7-[8-nitromethyl-7-(3-methyl-3-hydroxy-1-octenyl)-1,4-dioxaspiro[4.4]non-6-yl]-5-heptenoic acid in 4 ml. of tetrahydrofuran was treated at 0° C. with 0.4 ml. of concentrated hydrochloric acid and stirred at 0° C. for 1.5 hours. The reaction mixture was added to water and extracted with ether. After washing with water and drying over magnesium sulfate, the extract was evaporated and the residue chromatographed on silica. Elution with 15% ethyl acetate in hexane gave 0.11 g. of the title product as an oil, $\lambda_{max}^{film}$ 3.00 (shoulder), 3.50, 5.80, 6.45, 7.25, 10.30 μ. NMR: δ 1.32 (S, 15-methyl), 4.49 (M, 2, —CH$_2$NO$_2$), 5.80 (M, 4, olefinic —H), 5.92 (S, 2, OH) ppm. Mass spectrum: M$^+$ —H$_2$O at m/e 391.2402 (theory 391.2358).

EXAMPLE 60

7-[2-(3-Hydroxy-3-Phenyl-1-Octenyl)-3-Nitromethyl-5-Oxo-Cyclopentyl]-5-Heptenoic Acid A solution of 0.3 g. of 7-[8-nitromethyl-7-(3-hydroxy-3-phenyl-1-octenyl)-1,4-dioxaspiro[4.4]-non-6-yl]-5-heptenoic acid in 6 ml. of dry tetrahydrofuran was treated at 0° C. with 0.6 ml. of concentrated hydrochloric acid and stirred at 0° C. for 1.5 hours. The reaction mixture was added to water and extracted with ether. After washing with water and drying over magnesium sulfate, the extract was evaporated and the residue chromatographed on silica. Elution with 33% ethyl acetate in hexane gave 0.08 g. of the title product as an oil, $\lambda_{max}^{film}$ 3.00 (shoulder), 3.40, 5.75, 6.40, 7.20, 10.20, 13.20, 14.18 μ. NHR: δ 4.45 (m, 2, —CH$_2$NO$_2$), 5.40 (m, 2, 5 and 6—H), 5.85 (m, 2, 13 and 14—H), 5.90 (s, 2, OH), 7.40 (s, 5, aromatic —H) ppm. Mass spectrum: M$^+$ at m/e 471 (theory 471), M$^+$ —H$_2$O at m/e 453 (theory 453).

EXAMPLE 61

7-[3α-Cyano-2-(3-Hydroxy-3-Methyl-1-Octenyl)-5-Oxocyclopentyl]-5-Heptenoic Acid A solution of 0.30 g. of 7-[8α-cyano-7-(3-hydroxy-3-methyl-1-octenyl)-1,4-dioxaspiro[4.4]non-6-yl]-5-heptenoic acid in 12 ml. of THF was treated under nitrogen at 25° with 2.8 ml. of 3M perchloric acid and stirred for 6 hours. The reaction mixture was added to water and extracted with ether. After washing with brine and drying with magnesium sulfate, the ether extract was evaporated and the residue chromatographed on silica. Elution with 30% ethyl acetate in hexane gave 0.18 g. of the title product as an oil, $\lambda_{max}^{film}$ 3.0 (shoulder), 3.4, 4.45, 5.75, 8.75, 10.3 μ. NMR: δ 1.33 (S, 15-methyl), 5.54 (M, 2, 5 and 6—H), 5.82 (M, 2, 13 and 14—H), 6.70 (M, 2, —OH) ppm. Mass spectrum: M$^+$ at m/e 375 (theory 375), M$^+$—H$_2$O at m/e 357.2303 (theory 357.2314).

EXAMPLE 62

7-[3β-Cyano-2-(3-Hydroxy-3-Methyl-1-Octenyl)-5-Oxocyclopentyl]-5-Heptenoic Acid A solution of 0.8 g. of 7-[8β-cyano-7-(3-hydroxy-3-methyl-1-octenyl)-1,4-dioxaspiro[4.4]non-6-yl]-5-heptenoic acid in 16 ml. of THF was treated under nitrogen at 25° with 4 ml. of 3M perchloric acid and stirred for 10 hours. The reaction mixture was added to water and extracted with ether. After washing with brine and drying with magnesium sulfate, the ether extract was evaporated and the residue chromatographed on silica. Elution with 35% ethyl acetate in hexane gave 0.68 g. of the title product as an oil, $\lambda_{max}^{film}$ 2.95 (shoulder), 3.40 4.40, 5.75, 7.00, 8.50, 10.15 μ. NMR: δ 1.35 (S, 15-methyl), 3.40 (M, 1, 11—H), 5.49 (M, 2, 5 and 6—H), 5.88 (d, J=4, 13 and 14—H), 6.41 (S, 2, —OH) ppm. Mass spectrum: M$^+$ at m/e 375.2347 (theory 375.2409).

EXAMPLE 63

3α-Cyano-2-(3-Hydroxy-3-Methyl Octyl-5-Oxocyclopentyl Hepanoic Acid

A solution of 0.29 g. of 7-[3α-cyano-2-(3-hydroxy-3-methyl-1-octenyl)-5-oxocyclopentyl]-5-heptenoic acid in 15 ml. of ethyl acetate was added to a prehydrogenated mixture of 0.18 g. of 10% Pd/C in 15 ml. of ethyl acetate and the mixture hydrogenated at 25° and atmospheric pressure until 2 equivalents of hydrogen were absorbed. After filtering, the solution was evaporated and the residue chromatographed on silica. Elution with 30% ethyl acetate in hexane afforded 0.18 g. of the title product as an oil, $\lambda_{max}^{film}$ 3.0 (shoulder), 3.4, 4.4, 5.7, 6.75, 8.1, 8.55, 10.7 μ. NMR: δ 6.10 (S, 2, OH), 1.22 (S, 15—CH$_2$) ppm. Mass spectrum: M$^+$—H$_2$O at m/e 361.2579 (theory 361.2617).

EXAMPLE 64

3β-Cyano-2-(3-Hydroxy-3-Methyl-Octyl)-5-Oxocyclopentyl Heptanoic Acid

A solution of 0.18 g. of 7-[3β-cyano-2-(3-hydroxy-3-methyl-1-octenyl)-5-oxocyclopentyl]-5-heptanoic acid in 20 ml. of ethyl acetate was added to a prehydrogenated mixture of 0.08 g. of 10% Pd/C in 10 ml. of ethyl acetate and the mixture hydrogenated at 25° and atmospheric pressure until 2 equivalents of hydrogen were absorbed. After filtering, the solution was evaporated and the residue chromatographed on silica. Elution with 30% ethyl acetate in hexane afforded 0.15 g. of the title product as an oil, $\lambda_{max}^{film}$ 3.0 (shoulder), 3.45, 4.45, 5.80, 6.80, 8.60, 10.9 μ. NMR: δ 1.25 (S, 15-methyl), 3.41 (M, 1, 11—H), 6.10 (S, 2, —OH) ppm. Mass spectrum: M$^+$—H$_2$O at m/e 361.2601 (theory 361.2617).

EXAMPLE 65

7-[2β-[3S)-3-Hydroxy-Trans-1-Octenyl]-3α-Methyl-5-Oxo-1α-Cyclopentyl]-Cis-5-Heptenoic Acid and

7-[2β-[(3S)-3-Hydroxy-Trans-1-Octenyl]-3β-Methyl-5-Oxo-1α-Cyclopentyl]-Cis-5-Heptenoic Acid A solution of 3.0 g. of PGA$_2$ in 60 ml. of tetrahydrofuran (THF) was added dropwise to an ice-cooled mixture of 24 ml. of 3M methyl magnesium bromide and 5.0 g. of cuprous chloride in 120 ml. of THF and stirred at 0° for 1 hour. The mixture was added to aqueous ammonium chloride solution and extracted with ether. After washing with water and drying over magnesium sulfate, the extract was concentrated to give crystalline material. Filtration followed by recrystallization from ether-pentane afforded 1.2 g. of the first title product, m.p. 68°–70° C., $\lambda_{max}^{KBr}$ 3.0 (shoulder), 3.5, 5.8, 6.9, 7.6, 8.05, 8.55, 10.3 μ. NMR: δ 6.93 (s, 2, OH), 5.54 (m, 13 and 14—H), 5.38 (m, 5 and 6—H), 4.16 (m, 1, 15—H). Mass spectrum: M$^+$ at m/e 350.2476 (theory 350.2455).

Evaporation of the filtrates and silica chromatography of the residue with 30% ethylacetate in hexane followed by crystallization from ether-pentane gave 0.09 g. of the second title product, m.p. 72°–74° C., $\lambda_{max}^{film}$ 3.0 (shoulder), 3.5, 5.8 (shoulder), 5.9, 7.0, 8.15, 8.45, 10.4 μ. NMR: δ 7.05–6.22 (m, 2, OH), 5.48, (m, 4, olefinic), 4.15 (m, 1, 15—H) ppm. Mass spectrum: M+ at m/e 350.2460 (theory 350.2455).

EXAMPLE 66

2β-[(3S)-3-Hydroxyoctyl]-3α-Methyl-5-Oxo-1α-Cyclopentane Heptanoic Acid

A solution of 0.9 g. of 7-(2β-[(3S)-3-hydroxy-transoctenyl]-3α-methyl-5-oxo-1α-cyclopentyl)-cis-5-heptenoic acid in 10 ml. of methanol was added to a prehydrogenated mixture of 0.2 g. of 5% Pd/C in 155 ml. of methanol and the mixture hydrogenated at 25° and atmospheric pressure until two equivalents of hydrogen were absorbed. After filtering, the solution was evaporated and the residue chromatographed on silica. Elution with 25% ethylacetate in hexane followed by recrystallization from ethylacetate-hexane afforded 0.25 g. of the title product, m.p. 43.5°–44.5° C., $\lambda_{max}^{film}$ 3.0, 3.5, 5.8, 6.85, 8.5, 8.9 μ. NMR: δ 6.81 (s, 2, OH), 3.65 (m, 1, 15—H) ppm. Mass spectrum: M+ at m/e 354.2771 (theory 354.2768).

EXAMPLE 67

7-(5α-Hydroxy-2β-[(3S)-3-Hydroxy-Trans-1-Octenyl]-3α-Methyl-1α-Cyclopentyl)-Cis-5-Heptenoic Acid and 7-(5β-Hydroxy-2β-[(3S)-3-Hydroxy-1-Octenyl]-3α-Methyl-1α-Cyclopentyl)-Cis-5-Heptenoic Acid An ice-cooled solution of 7.8 g. of 7-(2β-[(3S)-3-hydroxy-trans-1-octenyl]-3α-methyl-5-oxo-1α-cyclopentyl)-cis-5-heptenoic acid in 150 ml. of methanol was treated with 3.5 g. of sodium borohydride and stirred at 0° C for 2 hour. The mixture was diluted with water and acidified with acetic acid. Extraction of the resulting mixture with ether, followed by washing, drying and evporation of the extract gave the crude product. Silica chromatography with 30% ethyl acetate in hexane afforded 3.5 g. of the first title product as an oil, $\lambda_{max}^{film}$ 3.0, 3.5, 5.85, 6.9, 7.15, 8.1, 8.9, 9.8, 10.35 μ. NMR: δ 5.57 (s, 3, OH), 6.0–5.17 (m, 4, olefinic), 4.21 (m, 2, 9 and 15—H), 1.01 (d, J=4.5, 11-methyl) ppm. Mass spectrum: M+ at m/e 352.2670 (theory 352.2613).

Further elution with 30% ethyl acetate in hexane afforded 3.0 g. of the second title product as an oil, $\lambda_{max}^{film}$ 3.0, 3.5, 5.85, 6.9, 7.15, 8.2, 10.4 μ. NMR: δ 5.61 (s, 3, OH), 5.52 (s, 4, olefinic), 4.10 (m, 2, 9 and 15—H), 0.91 (d, J=4.5, 11-methyl) ppm. Mass spectrum: M+ at m/e 352 (theory 352), M+—H$_2$O at m/e 334.2564 (theory 334.2507).

EXAMPLE 68

7-[8α-Cyano-7β-((3S)-3-Hydroxy-Trans-1-Octenyl)-1,4-Dioxaspiro[4.4]Non-6α-Yl]-Cis-5-Heptenoic Acid A solution of 10.0 g. of 7-[8-cyano-7-((3S)-3-hydroxy-trans-1-octenyl)-1,4-dioxaspiro[4.4]non-6α-yl]-cis-5-heptenoic acid and 13.0 g. of potassium t-butoxide in 700 ml. of t-butanol was stirred at 25° under nitrogen for 40 hours. The reaction mixture was diluted with water, acidified with acetic acid and extracted with ether. After washing and drying, the extract was evaporated and the residue chromatographed on silica. Elution with 35% ethyl acetate in hexane followed by recrystallization from ether-pentane gave 3.0 g. of the title product, m.p. 58.5°–61° C., $\lambda_{max}^{KBr}$ 3.0, 3.4, 5.8, 8.5, 8.9, 9.65, 10.3 μ. NMR+: δ 6.72 (S, 2, OH), 5.65 (M, 2, 13 and 14—H), 5.40 (M, 2, 5 and 6—H), 4.18 (M, 1, 15—H), 3.92 (S, 4, ketal) ppm. Mass spectrum: M+ at m/e 405.2492 (theory 405.2514).

EXAMPLE 69

7-[3α-Cyano-2-((3S)-3-Hydroxy-Trans-1-Octenyl)-5-Oxo-1α-Cyclopentyl]-Cis-5-Heptenoic Acid An ice-cooled solution of 0.5 g. of 7-[8α-cyano-7((3S)-3-hydroxy-trans-1-octenyl)-1,4-dioxaspiro[4.4]-non-6α-yl]-cis-5-heptenoic acid in 50 ml. of tetrahydrofuran was treated with 12.5 ml. of hydrochloric acid and stirred at 0° C. for 1 hour. The mixture was diluted with water, extracted with ether and the extract washed, dried and evaporated. Silica chromatography of the resulting residue with 35% ethyl acetate in hexane followed by recrystallization from ether-hexane gave 0.26 g. of the title product, m.p. 71°–73° C., $\lambda_{max}^{KBr}$ 3.0, 3.4, 5.7, 7.9, 8.55, 9.8, 10.3 μ. NMR: δ 7.0 (S, 2, OH), 5.82 (M, 2, 13 and 14—H), 5.50 (M, 2, 5 and 6—H), 4.28 (M, 1, 15—H) ppm. Calcd. for $C_{21}H_{31}O_4N$: C, 69.77; H, 8.63; N, 3.86. Found: C, 69.69; H, 8.83; N, 3.62.

EXAMPLE 70

3α-Cyano-2β-[(3S)-3-Hydroxyoctyl]-5-Oxo-1α-Cyclopentane Heptanoic Acid

A solution of 0.48 g. of 7-[3α-cyano-2-((3S)-3-hydroxy-trans-1octenyl)-5-oxo-1α-cyclopentyl]-cis-5-heptenoic acid in 20 ml. of ethyl acetate was added to a prehydrogenated suspension of 0.22 g. of 5% Pd/C in 20 ml. of ethyl acetate and hydrogenated at 25° C. and atmospheric pressure until 2 equivalents of hydrogen were absorbed. The reaction mixture was filtered, evaporated and chromatographed on 20% silver nitratedsilica. Elution with 50% ethyl acetate in hexane gave 0.164 g. of the title product, $\lambda_{max}^{film}$ 3.45 (shoulder), 3.4, 4.45, 5.75, 6.85, 7.1, 8.65 μ. NMR: δ 3.60 (M, 1, 15—H), 5.70 (S, 2, OH, removed with D$_2$O) ppm. Mass spectrum: M+ at m/e 365.2566 (theory 365.2566).

The subject matter which the applicants regard as their invention is particularly pointed out and distinctly claimed as follows:

1. A compound of the formula:

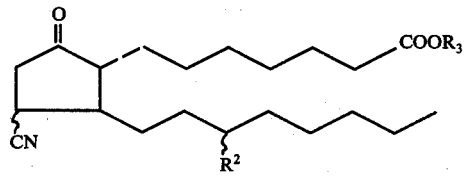

wherein R$^2$ is hydroxy, acetoxy or tetrahydropyranyloxy and R$_3$ is hydrogen or lower alkyl.

* * * * *